(12) United States Patent
Behrens

(10) Patent No.: US 7,442,195 B1
(45) Date of Patent: Oct. 28, 2008

(54) APPARATUS AND METHOD FOR THE REDUCTION OF BONE FRACTURES

(76) Inventor: Alfred F. Behrens, One Harwood Dr., Madison, NJ (US) 07940-2710

( * ) Notice: Subject to any disclaimer, the term of this patent is extended or adjusted under 35 U.S.C. 154(b) by 331 days.

(21) Appl. No.: 11/224,166

(22) Filed: Sep. 12, 2005

(51) Int. Cl.
*A61F 5/00* (2006.01)
*A61B 17/00* (2006.01)

(52) U.S. Cl. .................. 606/86 A; 606/167; 30/346

(58) Field of Classification Search ............... 606/82, 606/80, 81, 83, 84, 85, 99, 169, 179, 170, 606/178, 86 A; 30/346, 348, 353, 346.57
See application file for complete search history.

(56) References Cited

U.S. PATENT DOCUMENTS

| | | | |
|---|---|---|---|
| 4,969,888 A | | 11/1990 | Scholten et al. |
| 5,102,413 A | | 4/1992 | Poddar |
| 5,108,404 A | | 4/1992 | Scholten et al. |
| 5,383,888 A | * | 1/1995 | Zvenyatsky et al. ......... 606/206 |
| 5,549,637 A | * | 8/1996 | Crainich ..................... 606/207 |
| 5,702,408 A | * | 12/1997 | Wales et al. .................. 606/139 |
| 5,722,977 A | * | 3/1998 | Wilhelmy ..................... 606/84 |
| 5,972,015 A | | 10/1999 | Scribner et al. |
| 6,066,154 A | | 5/2000 | Reiley et al. |
| 6,679,886 B2 | * | 1/2004 | Weikel et al. ................. 606/79 |
| 6,726,691 B2 | | 4/2004 | Osorio et al. |
| 6,923,813 B2 | * | 8/2005 | Phillips et al. ............... 606/86 |

* cited by examiner

*Primary Examiner*—Pedro Philogene
(74) *Attorney, Agent, or Firm*—Arthur Jacob

(57) ABSTRACT

Reduction of a bone fragment of a bone fracture at a bone fracture site is accomplished through a minimally invasive access passage utilizing instruments having a working head actuated from a location remote from the bone fracture site, between an insertion configuration dimensioned and configured to present a minimal cross-sectional area for ready passage through the minimally invasive access passage and a working configuration dimensioned and configured to establish an essentially rigid working face of substantially greater cross-sectional area than the minimal cross-sectional area. The working head is actuated into the working configuration and manipulated from the remote location while in the working configuration to engage the working face with the bone fragment and manipulate the bone fragment into an anatomically appropriate reduced position at the bone fracture site.

20 Claims, 17 Drawing Sheets

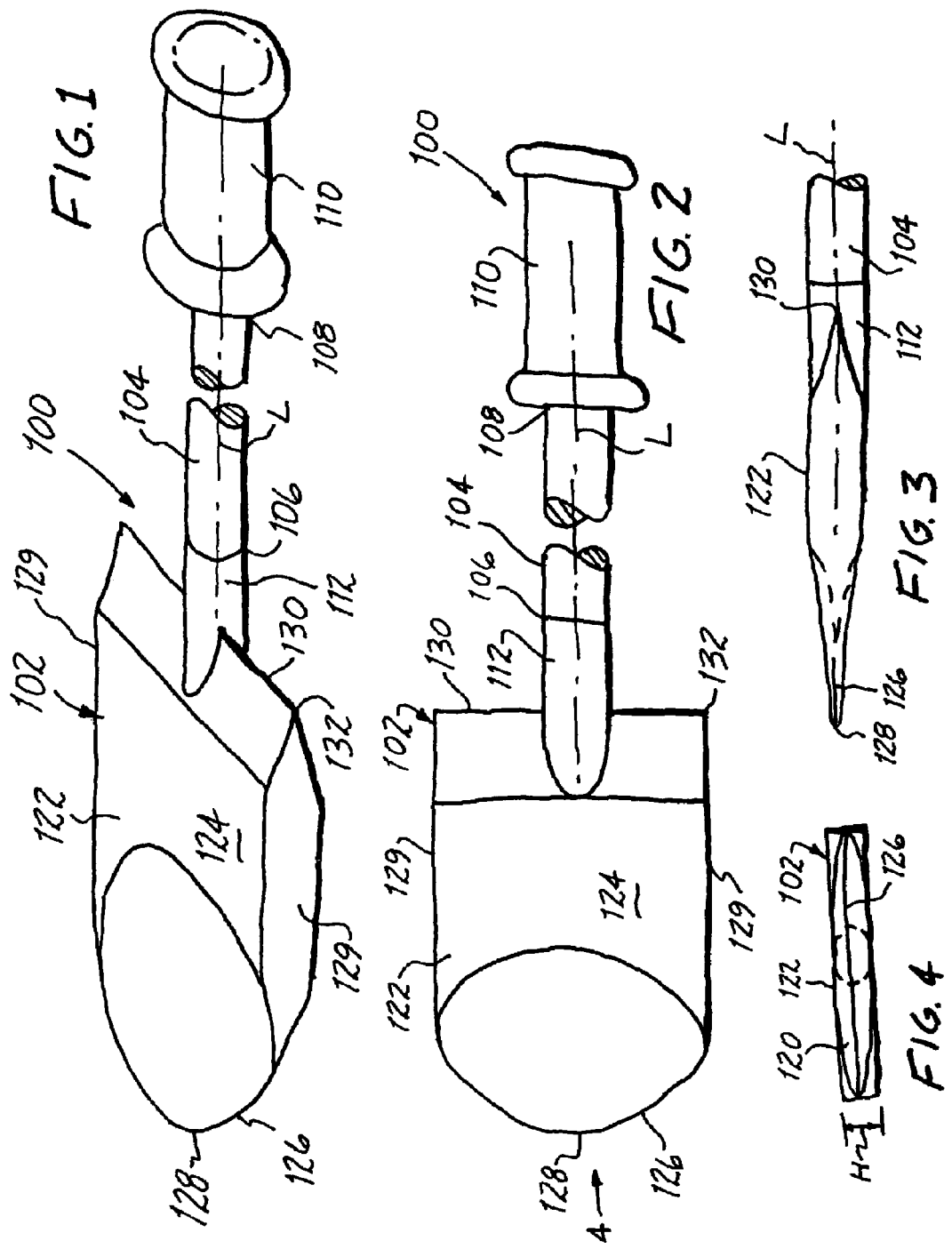

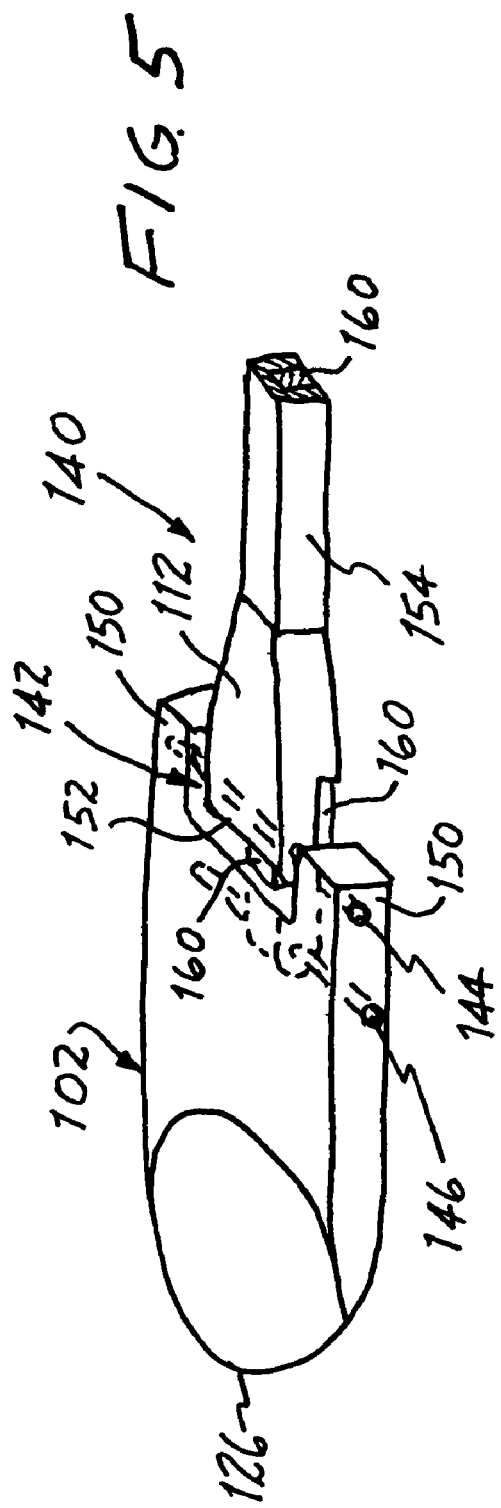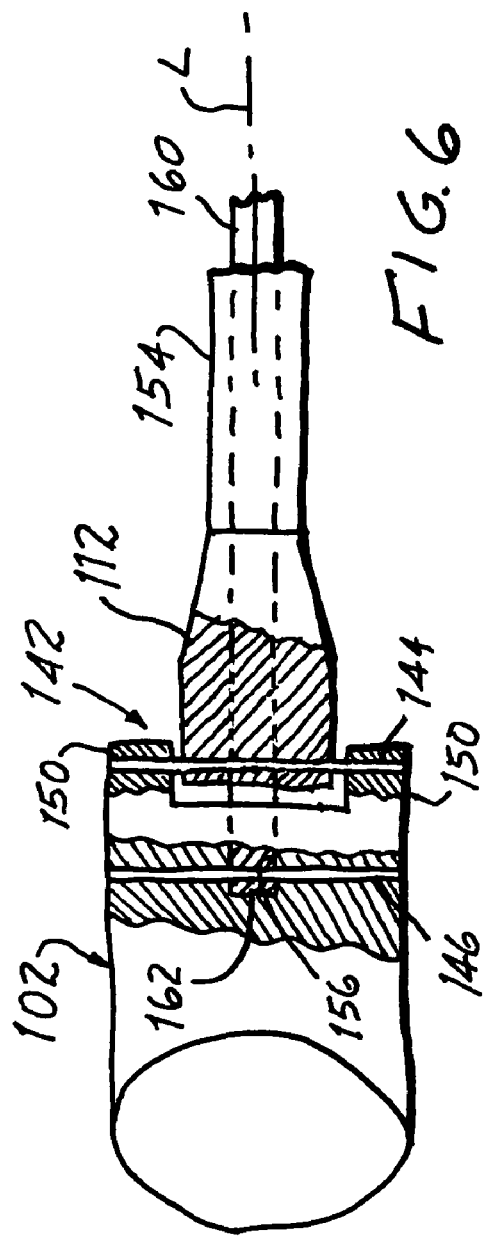

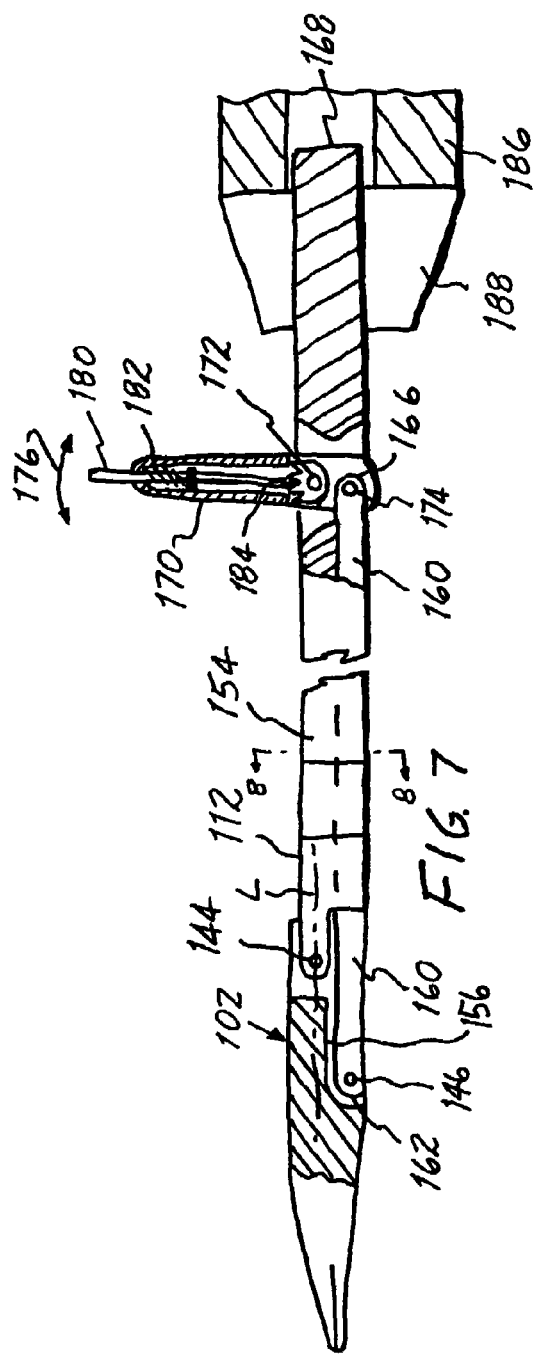
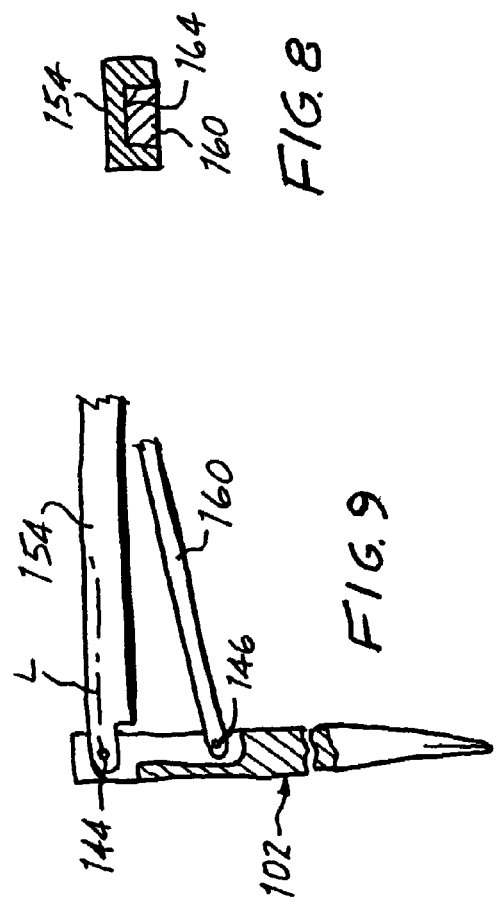

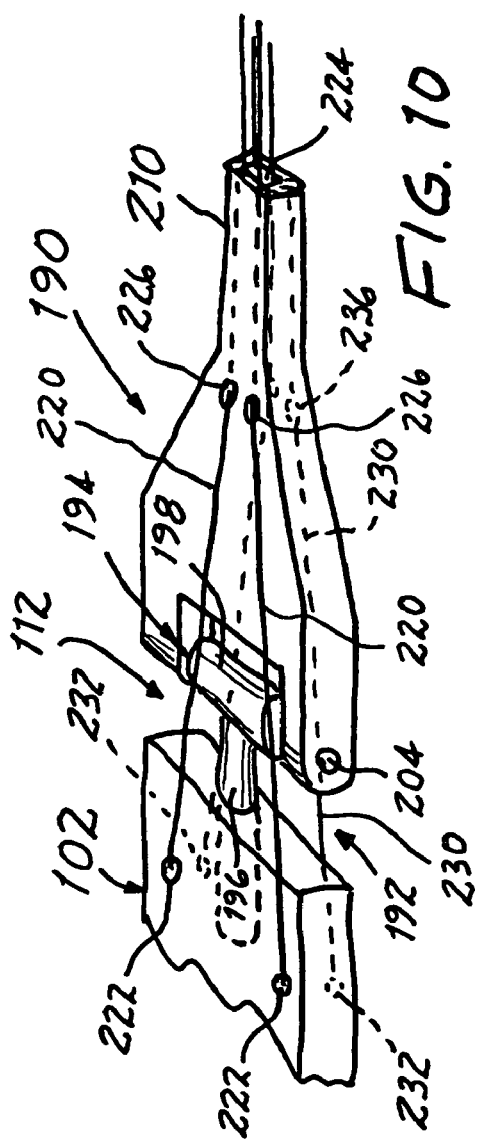
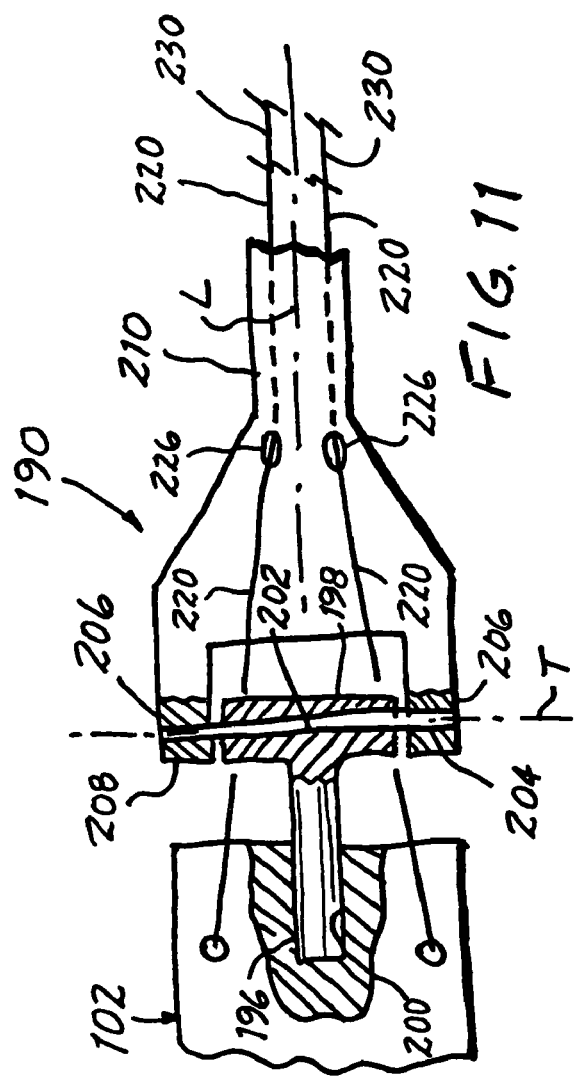

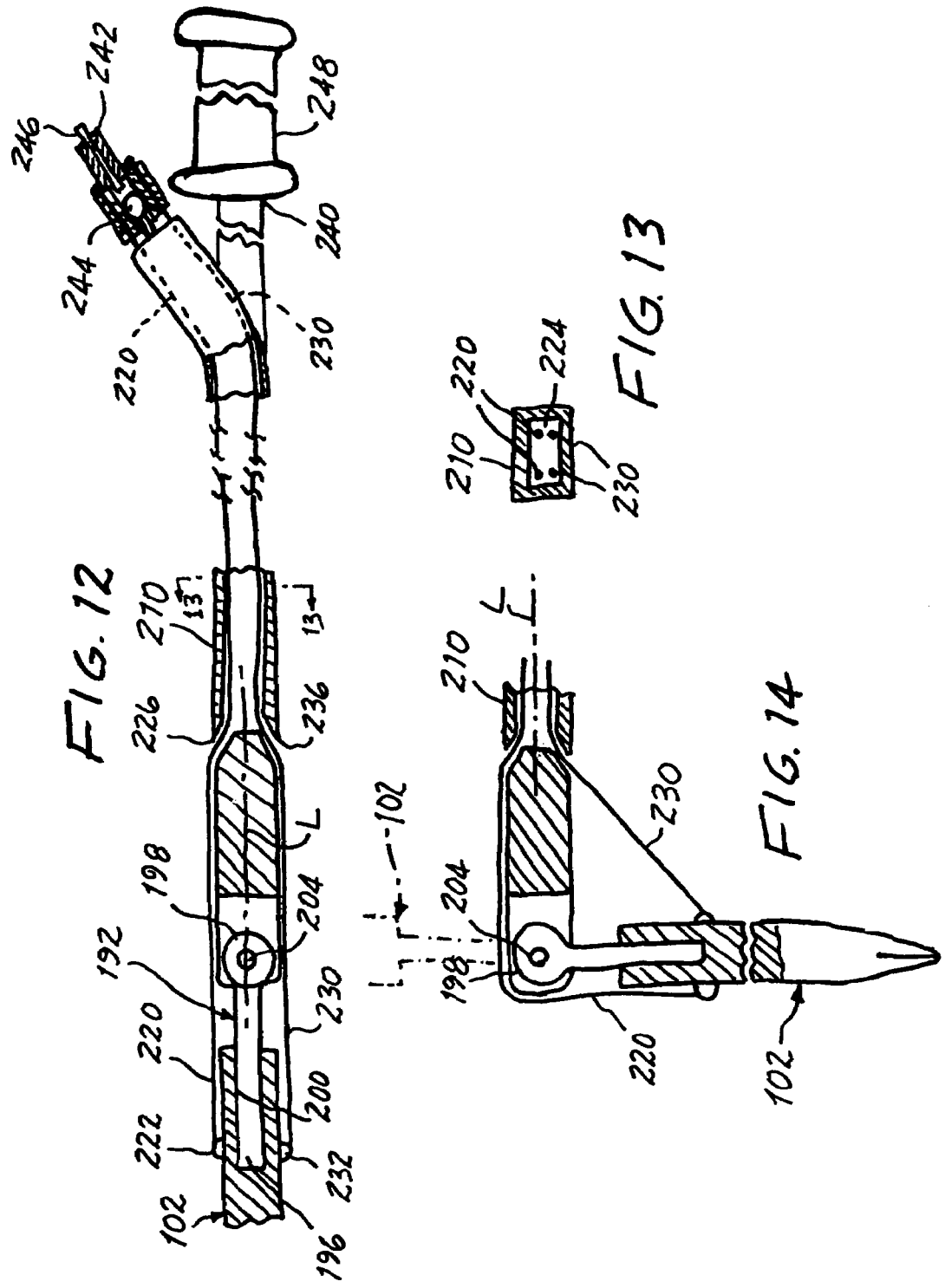

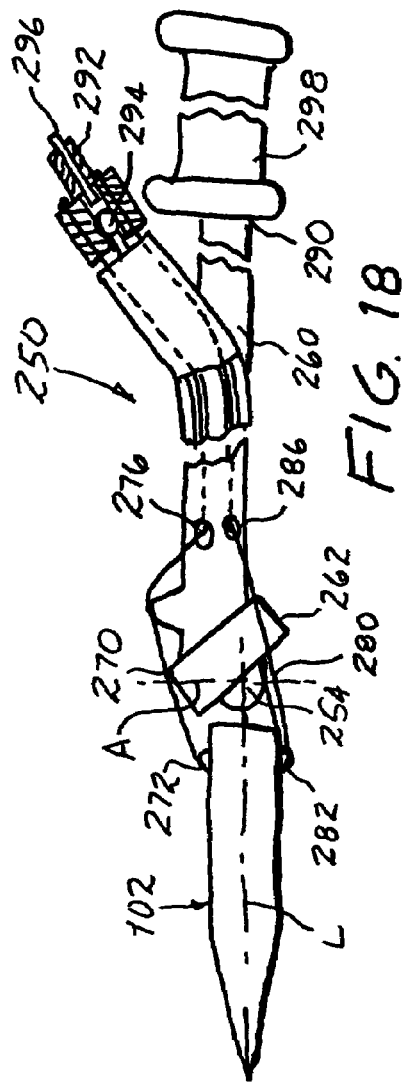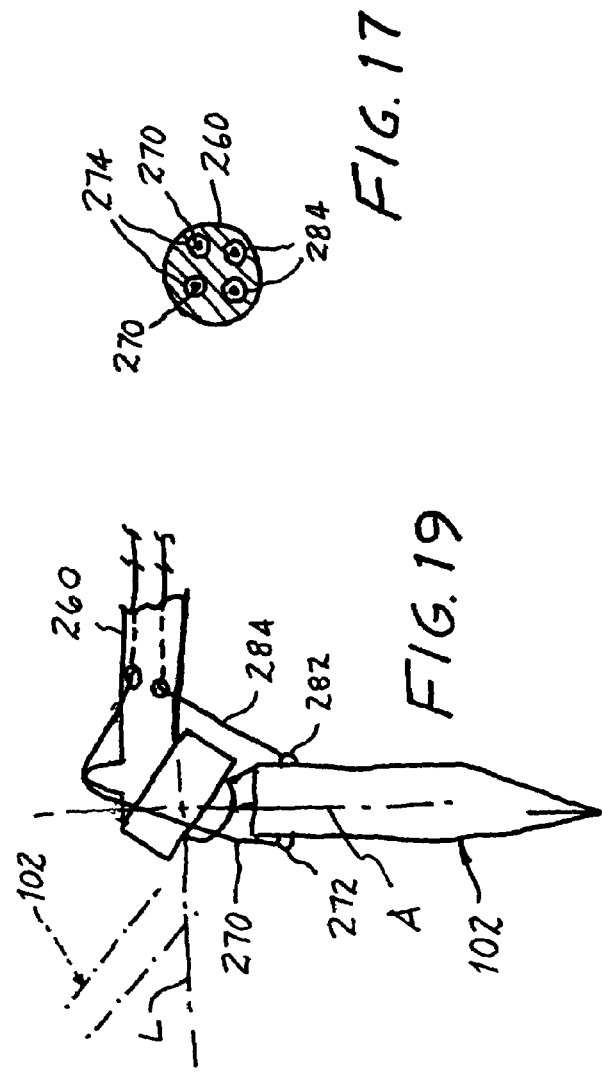

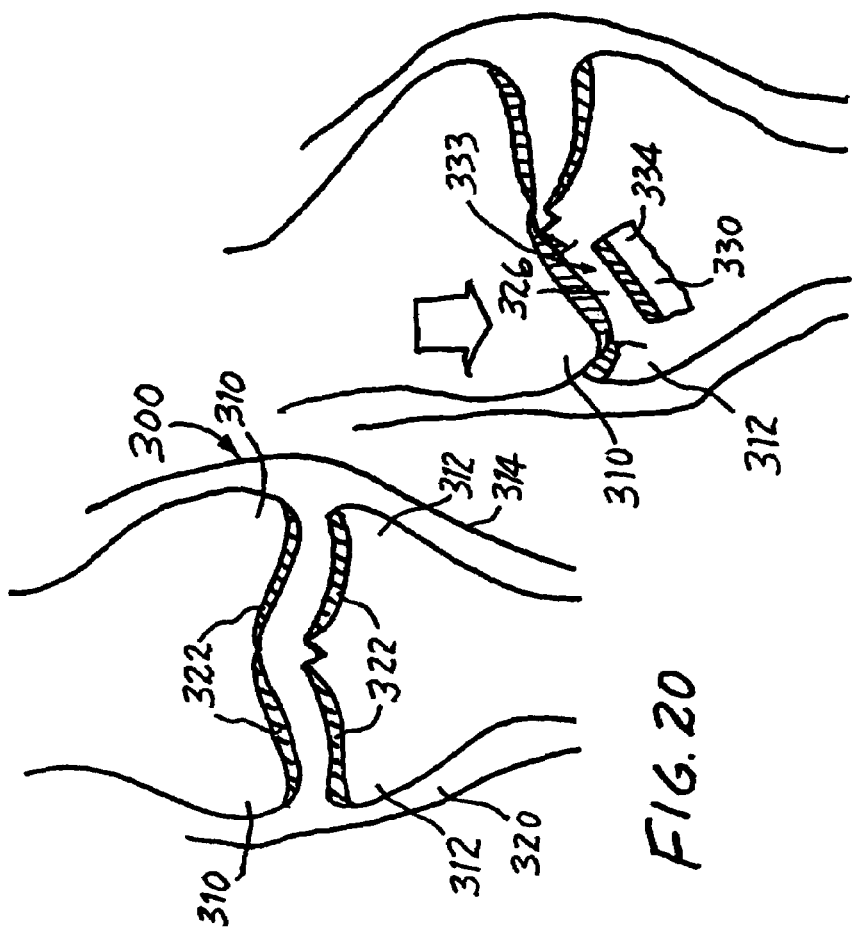
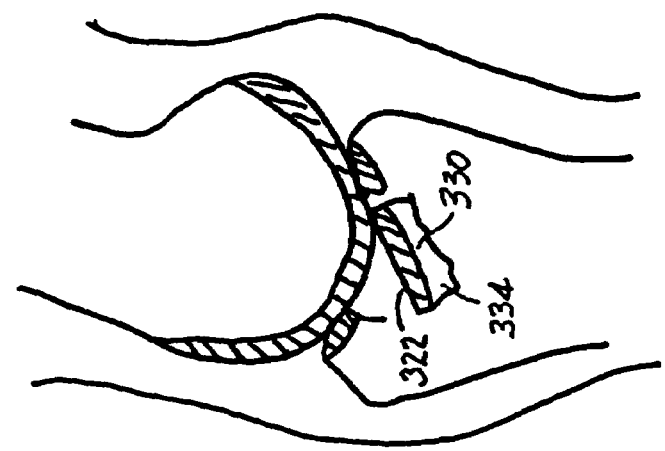
FIG. 20
FIG. 21
FIG. 22

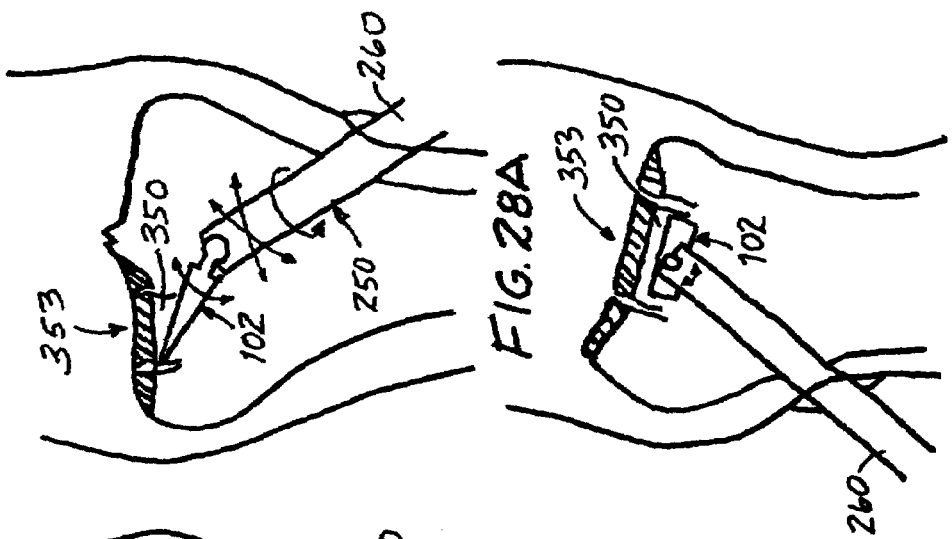
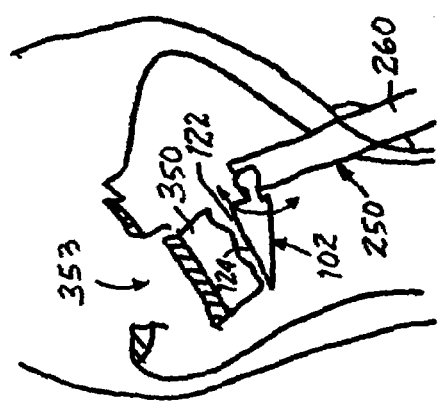
FIG. 27A
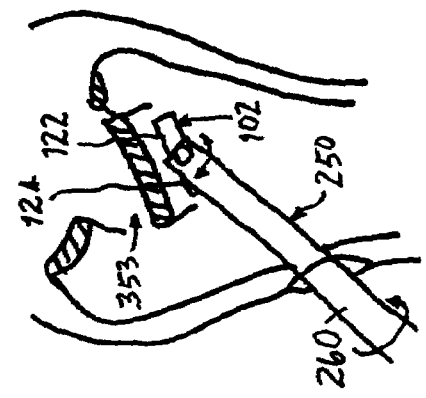
FIG. 27B
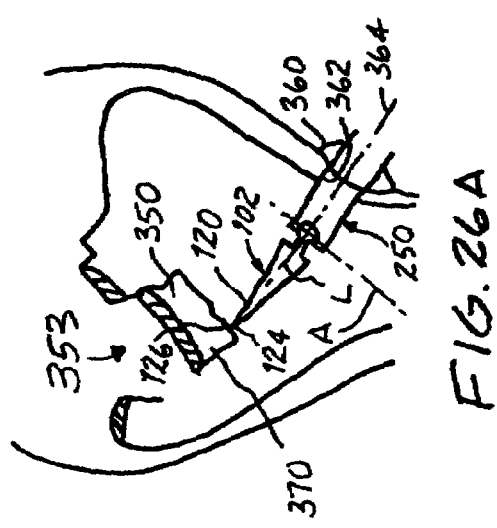
FIG. 26A
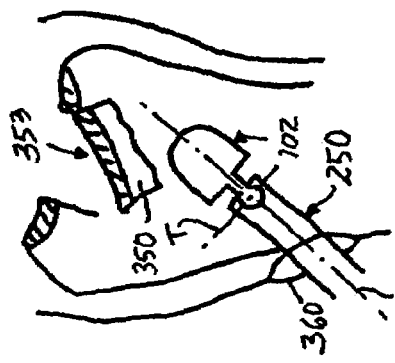
FIG. 26B

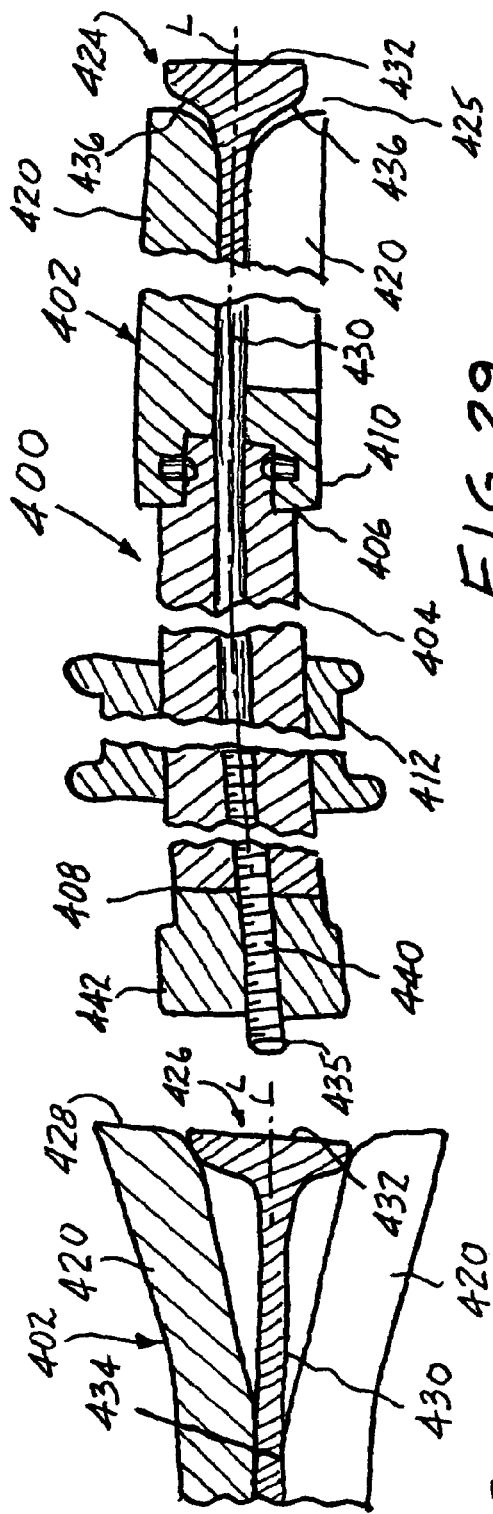
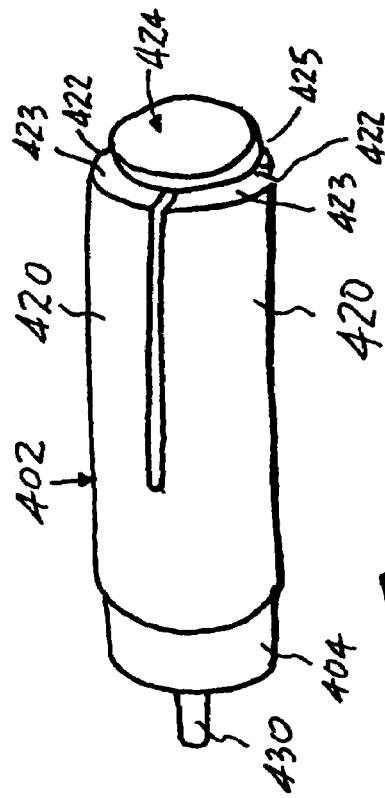
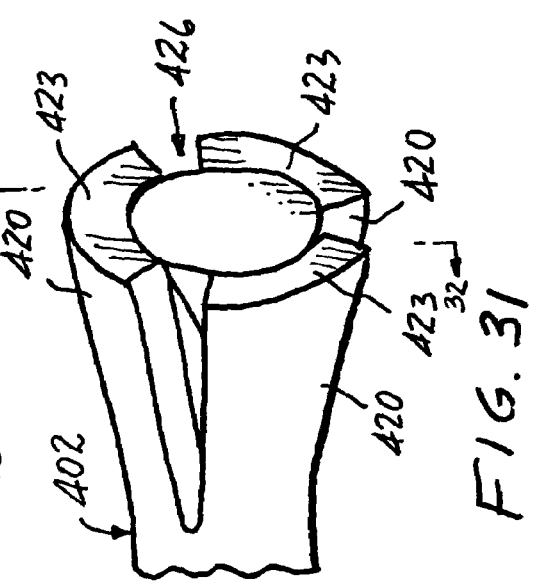

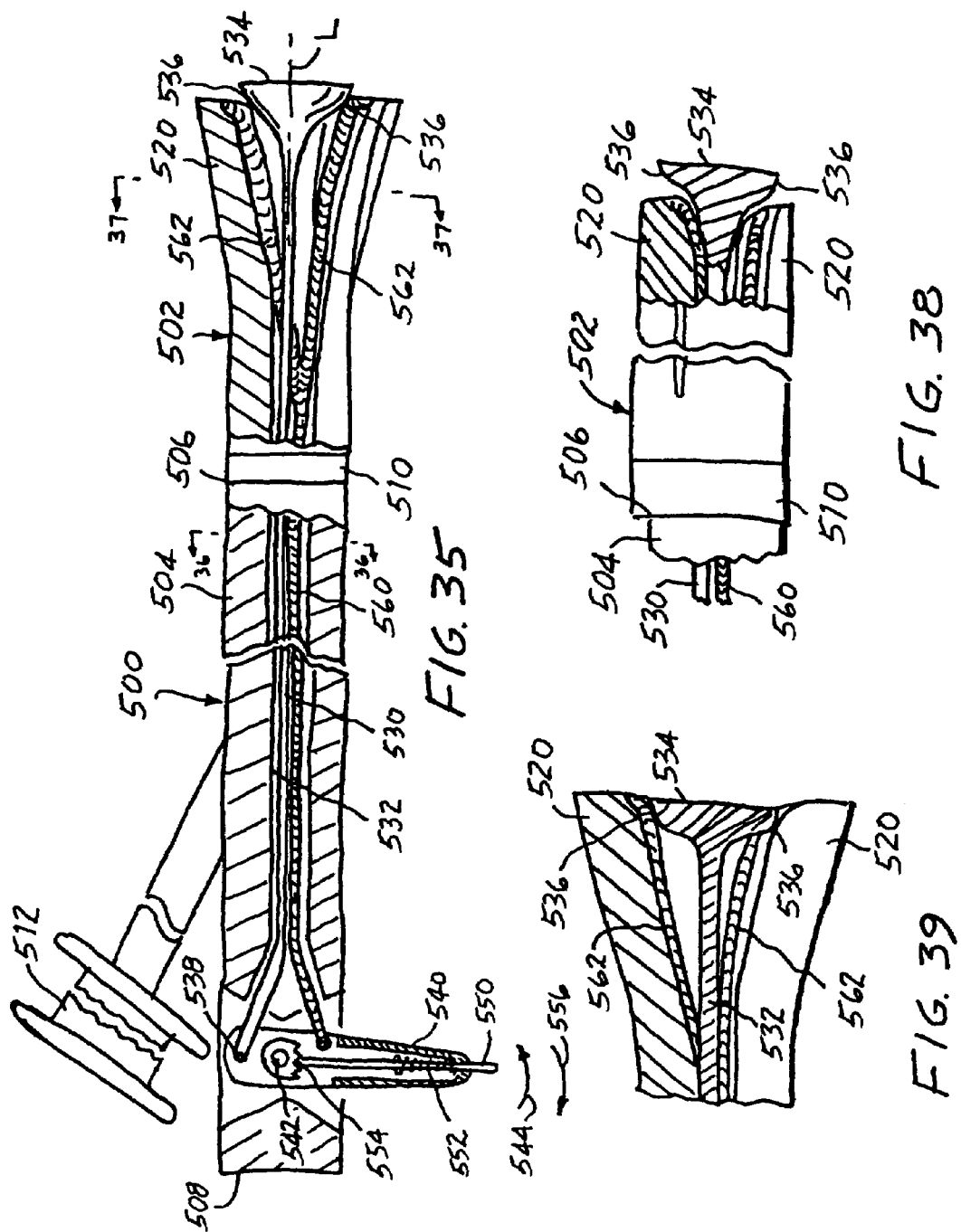

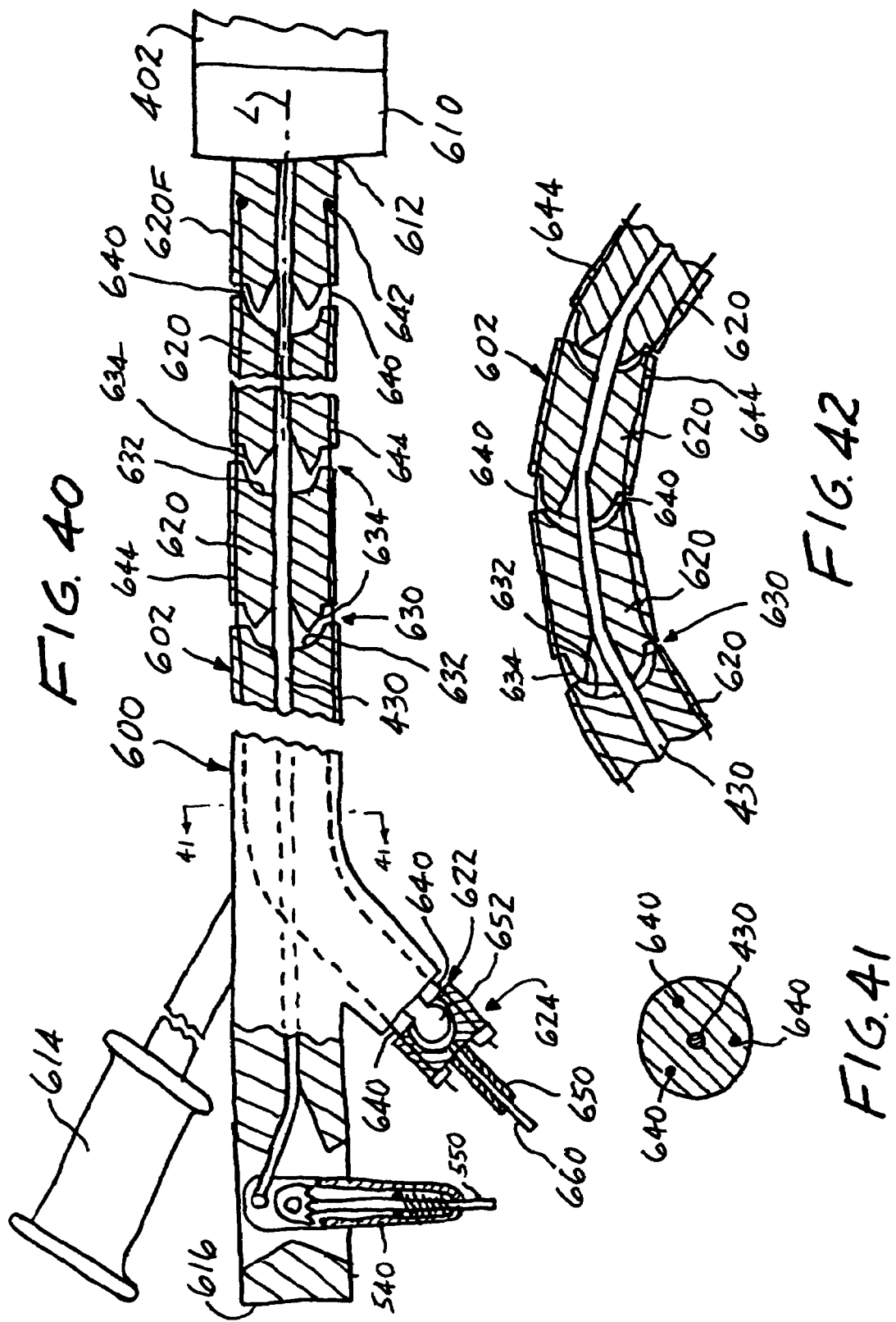

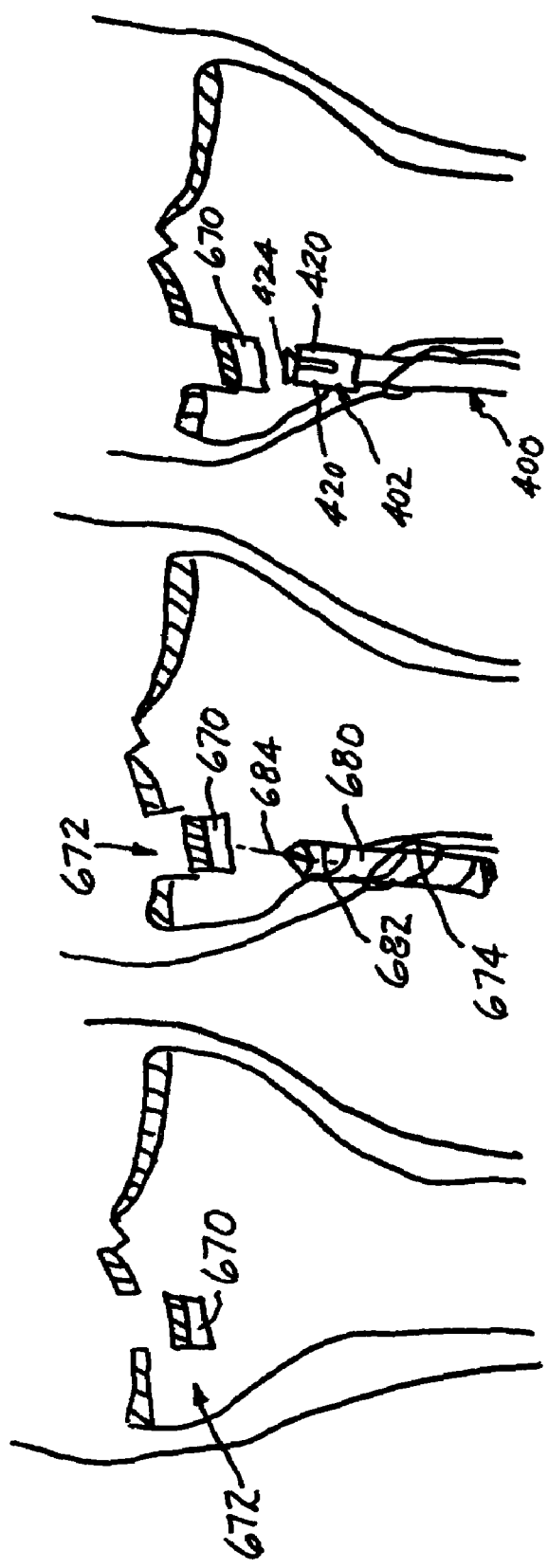

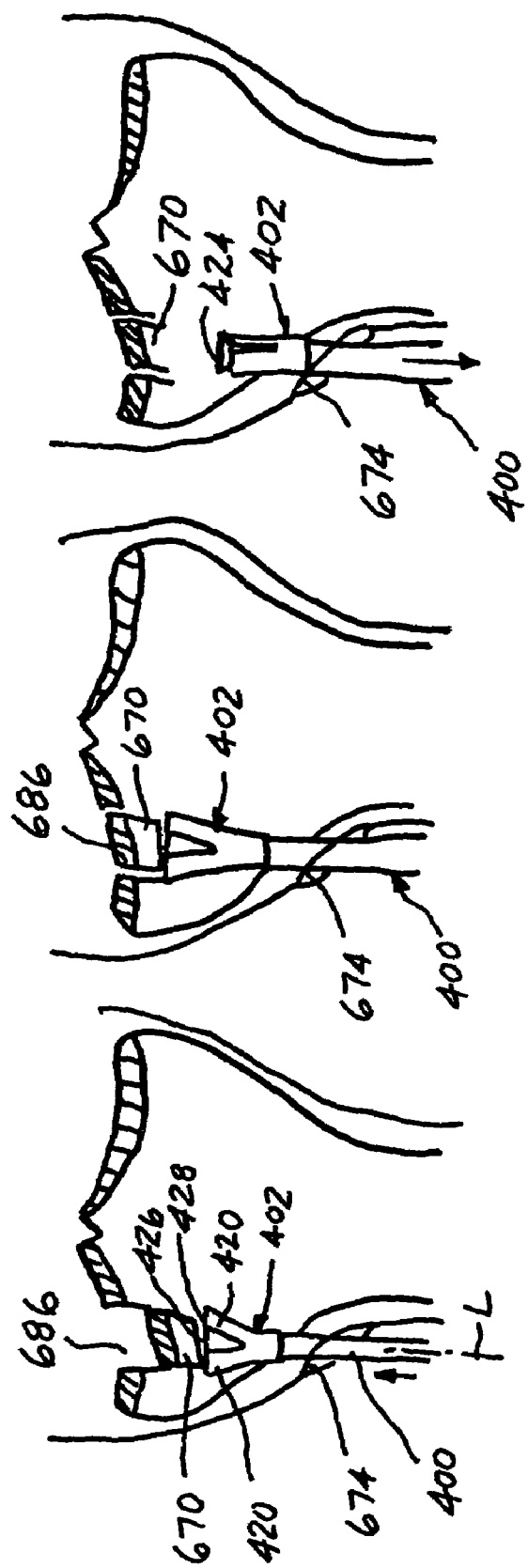

APPARATUS AND METHOD FOR THE REDUCTION OF BONE FRACTURES

BACKGROUND OF THE INVENTION

1. Field of the Invention

The present invention relates generally to the reduction of bone fractures and other bone conditions and pertains, more specifically, to instruments and techniques which allow such reduction to be accomplished with minimally invasive procedures. In particular, the instruments and techniques are used to manage bone fractures and bone conditions located near joints of the body (peri-articular fractures) and fractures that involve joint surfaces (intra-articular fractures).

2. Description of Related Art

Most joint related fractures require precise reduction and stabilization so as to avoid healing with a rough or misaligned joint surface which quickly can cause disabling post-traumatic arthritis. The majority of these intra-articular fractures currently are reduced under direct inspection of the bone fracture fragments, utilizing relatively large incisions to gain open access to the injured areas. The incisions extend into the joint and are carried through muscles, tendons and capsules in order to reach the fracture. Once exposed, the bone fracture fragments are physically disengaged from their displaced positions and are reduced as anatomically as possible, all under direct vision. These fragments then are fixed in the reduced position, as by wires, screws, plates and external fixators used either alone or in various combinations. Despite careful operative procedures, such open reduction carries substantial risks to the patient, ranging from soft tissue necrosis to deep wound and joint infections. Even where incisions heal well, scarring of the transected tissues is inevitable and can result in joint stiffness and potentially serious functional restrictions affecting daily living, as well as work and recreational pursuits.

More recent attempts at avoiding the drawbacks and risks of open reduction have involved techniques for the percutaneous reduction and affixation of bone fracture fragments, utilizing small cylindrical and flat-ended bone punches and pins inserted through relatively small soft tissue incisions and fracture gaps or even drill holes. Under arthroscopic or radiographic visualization, these instruments are used to manipulate bone fracture fragments into more anatomical positions where the fragments are stabilized with screws, plates or a combination of both screws and plates. Although these techniques can avoid some of the complications afflicting open reduction, to date such techniques have been successful only in the reduction of simple fractures, such as splits and some depressions.

The utilization of bone punches for the reduction and stabilization of bone fractures presents crucial shortcomings. Thus, bone punches permit only unidirectional motion and concomitant unidirectional movement of bone fracture fragments. Further, bone punches have relatively small contact, or working surfaces with which to engage bone fragments, usually no more than one square centimeter. As a result, when attempting to reduce bone fracture fragments, and especially comminuted bone fracture fragments, rather than pushing the bone fracture fragments into a desired position, bone punches tend to slide through gaps between the bone fracture fragments and penetrate into the joint itself, rendering the punches ineffectual and even potentially harmful to the joint. Larger diameter punches would require corresponding larger diameter bone openings for enabling introduction of the punches, presenting a danger of developing stress fractures at the level of the entry holes, such stress fractures being an unacceptable condition.

BRIEF SUMMARY OF THE INVENTION

The present invention provides instruments and method for enabling effective reduction of bone fractures utilizing minimally invasive techniques, thereby avoiding drawbacks of open reduction and current percutaneous procedures. As such, the present invention attains several objects and advantages, some of which are summarized as follows: Enables minimally invasive procedures for the reduction of bone fractures by virtue of requiring only small openings in soft tissue and bone for the introduction, manipulation and removal of instruments constructed for carrying out percutaneous techniques for bone fracture reduction; provides instruments having broad working configurations relative to narrow insertion configurations to accomplish effective support and movement of bone fracture fragments into reduced positions at a bone fracture site accessed through a minimally invasive access passage; allows for simplified manipulation of a working head from a remote location to rotate and translate bone fracture fragments in multiple directions for minimally invasive bone fracture reduction, and especially in the management of bone fractures and bone conditions located near joints of the body (peri-articular fractures) and fractures that involve joint surfaces (intra-articular fractures); allows the reduction of relatively large fractured joint surfaces, percutaneously, using only arthroscopic or radiographic visualization methods in minimally invasive procedures; avoids risks and complications which otherwise could arise out of open reduction procedures, such as soft tissue necrosis and bone infections; reduces operating times and blood loss; enables a reduction in the length of a hospital stay and, in some instances, avoids hospitalization entirely; reduces recovery time and patient discomfort; avoids excessive joint stiffness and potentially serious functional restrictions affecting daily living, as well as work and recreational pursuits.

The above objects and advantages, as well as further objects and advantages, are attained by the present invention which may be described briefly as apparatus for the reduction of a bone fragment of a bone fracture at a bone fracture site through a minimally invasive access passage to the bone fracture site, the access passage following an access direction and having a minimally invasive cross-sectional area, the apparatus comprising: a working head constructed for actuation between an insertion configuration and a working configuration; the insertion configuration providing the working head with an insertion area transverse to the access direction and being dimensioned and configured for passing through the minimally invasive cross-sectional area to move along the access passage to the bone fracture site; the working configuration providing the working head with an essentially rigid working face extending over a working area transverse to the access direction, the working area of the extended working face being substantially greater than the insertion area for engaging and manipulating the bone fragment into a reduced position; an actuating arrangement including an actuator remote from the working head for actuating the working head between the insertion configuration and the working configuration from an actuating site remote from the bone fracture site; a coupling arrangement coupling the actuator with the working head for enabling remote actuation of the working head in response to operation of the actuator; and a manipulating arrangement for selective manipulation of the working head from the remote actuating site such that insertion of the working head through the access passage to the bone fracture site is accomplished with the working head in the insertion configuration, and upon placement of the working head at the bone fracture site and actuation of the working head to the working configuration, reduction of the bone fragment is accomplished with the working head in the working configuration to engage the bone fragment with the working face and manipulate the bone fragment into the reduced position at the bone fracture site.

In addition, the present invention include apparatus for the reduction of a bone fragment of a bone fracture at a bone fracture site through a minimally invasive access passage to the bone fracture site, the access passage following an access direction and having a minimally invasive cross-sectional area, the apparatus comprising: a working head constructed for being moved between an insertion configuration and a working configuration; the insertion configuration providing the working head with an insertion area transverse to the access direction and being dimensioned and configured for passing through the minimally invasive cross-sectional area to move along the access passage to the bone fracture site; the working configuration providing the working head with an essentially rigid working face extending over a working area transverse to the access direction, the working area of the extended working face being substantially greater than the insertion area for engaging and maneuvering the bone fragment into a reduced position; and a manipulating arrangement including a manipulator for selective manipulation of the working head from a remote manipulating site such that insertion of the working head through the access passage to the bone fracture site is accomplished with the working head in the insertion configuration, and upon placement of the working head at the bone fracture site and movement of the working head in the working configuration, reduction of the bone fragment is accomplished with the working head in the working configuration to engage the bone fragment with the working face and maneuver the bone fragment into the reduced position at the bone fracture site.

Further, the present invention provides a method for the reduction of a bone fragment of a bone fracture at a bone fracture site through a minimally invasive access passage to the bone fracture site, the access passage following an access direction and having a minimally invasive cross-sectional area, the method comprising: introducing into the access passage a working head constructed for actuation between an insertion configuration and a working configuration; the insertion configuration providing the working head with an insertion area transverse to the access direction and being dimensioned and configured for passing through the minimally invasive cross-sectional area to move along the access passage to the bone fracture site; and the working configuration providing the working head with an essentially rigid working face extended over a working area transverse to the access direction, the working area of the extended working face being substantially greater than the insertion area for engaging and manipulating the bone fragment into a reduced position; with the working head in the insertion configuration, passing the working head through the minimally invasive cross-sectional area to move the working head along the access passage and place the working head at the bone fracture site; actuating an actuator remote from the working head to actuate the working head from the insertion configuration into the working configuration from an actuating site remote from the bone fracture site; and selectively manipulating the working head from the remote actuating site such that insertion of the working head through the access passage to the bone fracture site is accomplished with the working head in the insertion configuration and, upon placement of the working head at the bone fracture site and actuation of the working head to the working configuration, reduction of the bone fragment is accomplished with the working head in the working configuration to engage the bone fragment with the working face and manipulate the bone fragment into the reduced position at the bone fracture site.

BRIEF DESCRIPTION OF THE SEVERAL VIEWS OF THE DRAWING

The invention will be understood more fully, while still further objects and advantages will become apparent, in the following detailed description of preferred embodiments illustrated in the accompanying drawing, in which:

FIG. 1 is a somewhat diagrammatic fragmentary pictorial view of an instrument constructed in accordance with the present invention;

FIG. 2 is a fragmentary top plan view of the instrument;

FIG. 3 is a fragmentary side elevational view of the instrument;

FIG. 4 is and end view of the instrument, taken in the direction of the arrow in FIG. 2;

FIG. 5 is a somewhat diagrammatic fragmentary pictorial view of another instrument constructed in accordance with the invention;

FIG. 6 is a fragmentary top plan view of the instrument;

FIG. 7 is a side elevational view of the instrument;

FIG. 8 is a cross-sectional view taken along line 8-8 of FIG. 7;

FIG. 9 is a fragmentary side elevational view of the instrument, showing another operating configuration;

FIG. 10 is a somewhat diagrammatic fragmentary pictorial view of still another instrument constructed in a accordance with the invention;

FIG. 11 is a fragmentary top plan view of the instrument;

FIG. 12 is a side elevational view of the instrument;

FIG. 13 is a cross-sectional view taken along line 13-13 of FIG. 12;

FIG. 14 is a fragmentary side elevational view of the instrument, showing another operating configuration;

FIG. 17 is a cross-sectional view taken along line 17-17 of FIG. 16;

FIG. 18 is a side elevational view of the instrument;

FIG. 19 is a fragmentary side elevational view of the instrument, showing another operating configuration;

FIGS. 20 through 22 are diagrammatic illustrations of an intra-articular bone fracture;

FIGS. 26A through 28B are diagrammatic illustrations of another procedure for reduction of a bone fracture;

FIG. 29 is a longitudinal cross-sectional view of an alternate instrument constructed in accordance with the present invention;

FIG. 30 is a fragmentary end perspective view of the instrument;

FIG. 31 is a fragmentary end perspective view showing component parts in another operative configuration;

FIG. 32 is a fragmentary cross-sectional view taken along line 32-32 of FIG. 31;

FIG. 35 is a longitudinal cross-sectional view of another instrument constructed in accordance with the invention;

FIG. 38 is a fragmentary cross-sectional view of the instrument in one operating configuration;

FIG. 39 is a fragmentary view similar to FIG. 38, with the instrument in another operating configuration;

FIG. 40 is a longitudinal cross-sectional view showing an alternate construction for the instrument;

FIG. 41 is a transverse cross-sectional view taken along line 41-41 of FIG. 40;

FIG. 42 is a fragmentary longitudinal cross-sectional view showing the instrument in an another operating configuration;

FIGS. 43 through 48 are diagrammatic views illustrating a procedure for the reduction of a bone fracture, conducted in accordance with the present invention.

DETAILED DESCRIPTION OF THE INVENTION

Figure 15:
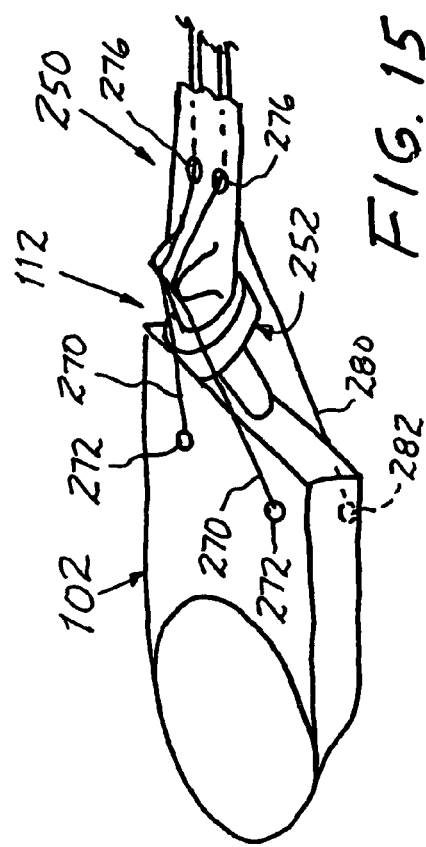
FIG. 15 is a somewhat diagrammatic fragmentary pictorial view of another instrument constructed in accordance with the invention.

Referring now to the drawing, and especially to FIGS. 1 through 4, an instrument constructed in accordance with the present invention is illustrated at 100 and is seen to have a working head 102 and a stem 104, the stem 104 extending along a longitudinal axis L between a first end 106 connected to the working head 102 and a second end 108 remote from the working head 102. A handle 110 at the remote second end 108 enables manipulation of the instrument 100, while a connection 112 connects the working head 102 to the first end 106 of the stem 104 for selective articulation of the working head 102 relative to the stem 104, all as will be described in greater detail below.

Working head 102 has an insertion area 120 transverse to the direction which extends along the longitudinal axis L, and an essentially rigid working face 122 extending over a working area 124, the working area 124 being substantially greater than the insertion area 120, providing the working head 102 with a generally blade-like overall configuration having a sharp cutting edge 126 extending along a forward edge 128 of the working head 102 in a lateral direction between laterally opposite side edges 129 of the working head 102 such that the working head 102 is provided with a broad, essentially flat working area 124 relative to the narrow, relatively small transverse dimensions of the stem 104 and the very limited altitudinal thickness H of the blade-like working head 102. In a preferred construction, the stem 104 has a generally cylindrical cross-sectional configuration, the working head 102 includes a further cutting edge 130 extending laterally along a rearward edge 132 of the working head 102, all for purposes set forth hereinafter. Working head 102 is constructed of a rigid material, such as a metal or a renitent or reinforced synthetic polymeric material, or various combinations of such materials, for establishing rigidity at working face 122 to enable engagement with and manipulation of bone fracture fragments, as described below. In addition, substantially rigid radiolucent materials are available for constructing the working head 102, and the choice of such a material will facilitate a visualization of reduced bone fragments during the course of a procedure, as described below.

Turning now to FIGS. 5 through 9, in one instrument 140 constructed in accordance with the present invention, the connection 112 provides for articulation between the working head 102 and the stem 104 and is a pivotal connection in the form of a hinged connection 142 comprising an upper hinge pin 144 and a lower hinge pin 146. Hinge pin 144 is seated within ears 150 extending longitudinally rearwardly along working head 102 and ears 150 are spaced apart laterally such that hinge pin 144 spans the distance between the ears 150 and passes through a headed end 152 of a stem 154 which extends longitudinally along longitudinal axis L. Hinge pin 146 is seated within working head 102 forward and slightly below hinge pin 144, hinge pin 146 spanning a slot 156 within working head 102 to pass through a link 160 having a forward end 162 extending into slot 156. Link 160 is placed within a longitudinal channel 164 of the stem 154, in sliding engagement with the stem 154, and includes a rearward end 166 adjacent remote end 168 of the stem 154.

An actuating arrangement includes an actuator in the form of a lever 170 mounted upon the stem 154 for selective pivotal movement about a pivot pin 172 adjacent the remote end 168 of the stem 154. Link 160 is pinned at 174 to lever 170 such that upon selective pivotal movement of lever 170 in forward and backward directions, as illustrated by arrow 176 in FIG. 7, the coupling arrangement provided by the hinged connection 142 and the link 160 moves the working head 102 between a first or insertion position, wherein the working head 102 is aligned with longitudinal axis L, as shown in FIGS. 5 through 7, and a second or working position, wherein the working head 102 extends transverse to longitudinal axis L, as illustrated in FIG. 9. A locking mechanism includes a lock bar 180 biased by a spring 182 into engagement with one of several notches 184 fixed relative to stem 154 so that lever 170, and consequently working head 102, is secured selectively in any one of several working positions between, and even beyond, the illustrated first and second positions of working head 102. A manipulating arrangement includes a manipulating handle 186 attached to the remote end 168 of the stem 154, as by selectively engagable and disengagable chuck jaws 188, for purposes described in greater detail below.

Another instrument constructed in accordance with the present invention is shown at 190 in FIGS. 10 through 14. Here, the connection 112 provides for articulation between the working head 102 and a stem and is a pivotal connection in the form of a hinged connection 192 comprising a generally T-shaped hinge member 194 having a post 196 and an integral sleeve 198. Post 196 is received within a complementary recess 200 in working head 102 so that the working head 102 is journaled for rotation about longitudinal axis L. Sleeve 198 includes a bore 202 through which a hinge pin 204 is passed, hinge pin 204 being anchored within opposed ears 206 at a forward end 208 of a stem 210, and complementary to bore 202 such that working head 102 is journaled for rotation about an axis T which extends transverse to axis L in lateral directions.

Altitudinally upper control cables 220 are attached to working head 102 at respective upper attachment points 222 and extend rearwardly to enter a conduit 224 within stem 210, through respective upper entrances 226. Similarly, altitudinally lower control cables 230 are attached to working head 102 at respective lower attachment points 232 and extend rearwardly to enter conduit 224 through respective lower entrances 236.

An actuating arrangement includes an actuator located adjacent remote end 240 of stem 210, the actuator being in the form of a control lever 242 mounted upon the stem 210 by means of a ball joint 244 and coupled to the upper and lower control cables 220 and 230, respectively, such that manipulation of the control lever 242 will move the control cables 220 and 230 selectively in forward and backward directions relative to the stem 210, in a differential manner commonly known as a "joy stick" arrangement. Thus, pulling the lower control cables 230 in a rearward direction while allowing the upper control cables 220 to move in a forward direction will pivot the working head 102 about hinge pin 204 to move the working head 102 from a position where the working head 102 is aligned with longitudinal axis L, as seen in FIGS. 10 through 12, through transverse positions located altitudinally between, and even beyond, the aligned position and an altitudinally downward transverse position, as illustrated in full lines in FIG. 14. Altitudinally upward transverse positions are accomplished merely by rotating the stem 210 about the longitudinal axis L. Alternately, upward transverse positions are attained by pulling the upper control cables 220 in a rearward direction while allowing the lower control cables 230 to move in a forward direction so as to pivot the working head 102 about hinge pin 204 to move the working head 102 from a position where the working head 102 is aligned with longitudinal axis L, as seen in FIGS. 10 through 12, through transverse positions located altitudinally between the aligned position and an altitudinally upward transverse position, as illustrated in phantom in FIG. 14.

Rotation of the working head 102 upon post 196, while the working head is in an altitudinally downward transverse orientation, is attained by pulling one of the lower control cables 230 rearwardly while allowing the other of the lower control cables 230 to move forward. Likewise, rotation of the working head 102 upon post 196, while the working head is in an altitudinally upward transverse orientation, is attained by pulling one of the upper control cables 220 rearwardly while allowing the other of the upper control cables 220 to move forward. A lock bar 246 selectively locks the ball joint 244 against inadvertent movement to hold the selected orientation of the working head 102 relative to the stem 210. A handle 248 is placed at the remote end 240 of stem 210 for manipulating instrument 190, as will be described below.

Turning now to FIGS. 15 through 19, in another instrument 250 constructed in accordance with the present invention, the connection 112 which provides for articulation between the working head 102 a stem is a pivotal connection in the form of a ball joint connection 252 comprising a generally spherical member 254 integral with the working head 102 and captured within a congruent socket 256 at the forward end 258 of a stem 260 extending along a longitudinal axis L, by a collar 262 threaded onto the forward end 256. The collar 262 itself includes an inner surface 264 having a generally part-spherical configuration.

Altitudinally upper control cables 270 are attached to working head 102 at respective upper attachment points 272 and extend rearwardly to enter respective conduits 274 within stem 260, through respective upper entrances 276. Similarly, altitudinally lower control cables 280 are attached to working head 102 at respective lower attachment points 282 and extend rearwardly to enter respective counterpart conduits 284 through respective lower entrances 286.

Figure 16:
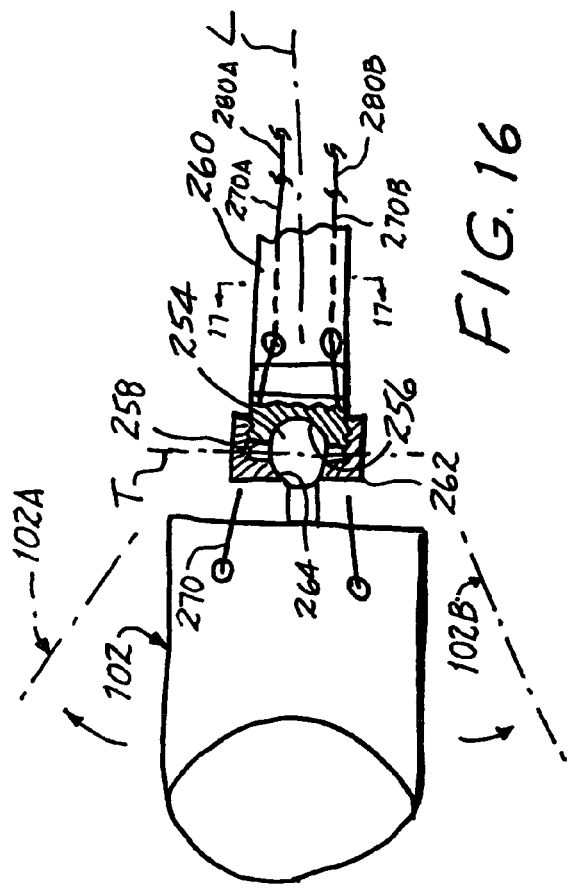
FIG. 16 is a fragmentary top plan view of the instrument.

An actuating arrangement includes an actuator located adjacent remote end 290 of stem 260, the actuator being in the form of a control lever 292 mounted upon the stem 260 by means of a ball joint 294 and coupled to the upper and lower control cables 270 and 280, respectively, such that manipulation of the control lever 292 will move the control cables 270 and 280 selectively in forward and rearward directions relative to the stem 260, in a differential manner commonly known as a "joy stick" arrangement. Thus, pulling the lower control cables 280 in a rearward direction while allowing the upper control cables 270 to move in a forward direction will pivot the working head 102 about a transverse axis T to move the working head 102 from a position where the working head 102 is aligned with longitudinal axis L, as seen in FIGS. 15, 16 and 18, through transverse positions located altitudinally between, and even beyond, the aligned position and an altitudinally downward transverse position, as illustrated in FIG. 19. Altitudinally upward transverse positions are accomplished by pulling the upper control cables 270 in a rearward direction while allowing the lower control cables 280 to move in a forward direction so as to pivot the working head 102 about transverse axis T to move the working head 102 from a position where the working head 102 is aligned with longitudinal axis L, as seen in FIGS. 15 and 18, through transverse positions located altitudinally between, and even beyond, the aligned position and an altitudinally upward transverse position, illustrated in phantom in FIG. 19.

Rotation of the working head 102 about an altitudinal axis A, while the working head is in an altitudinally downward transverse orientation, is attained by pulling one of the lower control cables 280 rearwardly while allowing the other of the lower control cables 280 to move forward. Likewise, rotation of the working head 102 about altitudinal axis A, while the working head is in an altitudinally upward transverse orientation, is attained by pulling one of the upper control cables 270 rearwardly while allowing the other of the upper control cables 270 to move forward. A lock bar 296 selectively locks the ball joint 294 against inadvertent movement to hold the selected orientation of the working head 102 relative to the stem 260.

In addition, rotation of the working head 102 about the altitudinal axis A while the working head 102 is aligned with longitudinal axis L, in the position shown in FIGS. 15 and 16, is accomplished by pulling rearwardly the one upper control cable 270A and the one lower control cable 280A located adjacent one side of longitudinal axis L while allowing the other upper control cable 270B and the other lower control cable 280B located adjacent the other side of longitudinal axis L to move forward, thereby rotating the working head to skewed positions, one of which is illustrated in phantom at 102A in FIG. 16. Likewise, rotation of the working head to skewed positions such as that illustrated in phantom at 102B in FIG. 16 is accomplished by pulling control cables 270B and 280B rearwardly while allowing control cables 270A and 280A to move forward. Further, combinations of control cable differential movements through manipulation of control lever 292 enable selective movement of working head 102 through infinite orientations about axes L, T and A. A handle 298 enables manipulation of instrument 250, as described below.

Referring now to FIGS. 20, 21 and 22, an example of a joint is shown in the form of a knee joint illustrated diagrammatically at 300 and seen to include femoral condyles 310 which engage corresponding tibial plateaus 312 during articulation of the knee joint 300. The knee joint 300 is surrounded by soft tissue, in particular, skin 314 and subcutaneous tissue 320. Layers 322 of articular cartilage facilitate normal articulation of the knee joint 300.

Typically, joint fractures occur when extreme external force applied to one of the bones of a joint causes an impact which breaks a corresponding bone of the joint. In the example shown in FIGS. 21 and 22, a femoral condyle 310 has impacted upon a corresponding tibial plateau 312, causing an intra-articular fracture at 326 in which a bone fracture fragment 330 has been broken away and displaced from its original anatomical position in the joint 300. The bone fracture site 333 is illustrated in both an anterior-posterior projection (FIG. 21) and a lateral projection (FIG. 22) and shows the bone fracture fragment 330 displaced and rotated from its original position by several centimeters, and wedged firmly within underlying bone. The bone fracture fragment 330 itself includes a portion of a cartilage layer 322 as well as some attached subchondral bone 334. Repair of the bone fracture 326 requires that the bone fracture fragment 330 be returned to an appropriate anatomical position, usually within two to three millimeters of its original anatomical position, in order to avoid severe, disabling arthritis which otherwise could ensue. It is therefore the objective of a reduction procedure to return the bone fracture fragment 330 as closely as possible to its optimal anatomical position and thereby avoid the development of post traumatic arthritis. Current open reduction procedures are prone to substantial morbidity. Further, current percutaneous methods are suitable only for the most simple fractures and are severely limited with respect to the size and maneuverability of the working surfaces of currently available instruments. The present invention enables minimally invasive procedures which avoid the drawbacks of open reduction and the limitations of current percutaneous procedures.

Figure 23:
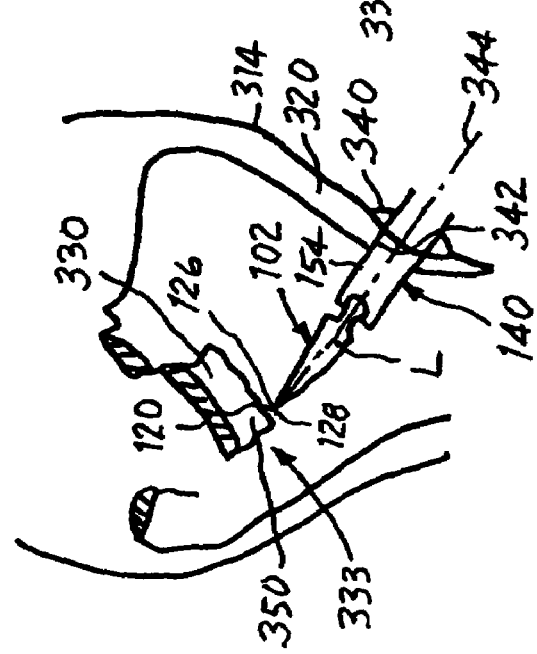

In accordance with a minimally invasive procedure of the present invention, the exact location and orientation of the bone fracture fragment 330 and the optimal approach for reduction of the bone fracture fragment 330 at bone fracture site 333 is determined by radiographs in two perpendicular planes, or by alternate imaging methods, which provide images similar to those represented in FIGS. 21 and 22. Alternately, arthroscopic procedures may be employed. Then, as seen in FIG. 23, a small incision 340 is made through skin 314 and subcutaneous tissue 320, opposite to the bone fracture fragment 330 to create an access passage 342 having a minimally invasive cross-sectional area and aligned with an access direction 344 leading to the bone fracture site 333. Instrument 140 is inserted into the incision 340, with the working head 102 in an insertion configuration wherein the working head 102 is aligned with longitudinal axis L and the insertion area 120 is oriented transverse to the access direction 344, the insertion area 120 being dimensioned and configured for passing through the minimally invasive cross-sectional area of the access passage 342 to move along the access passage 342 to the bone fracture site 333.

Figure 25:
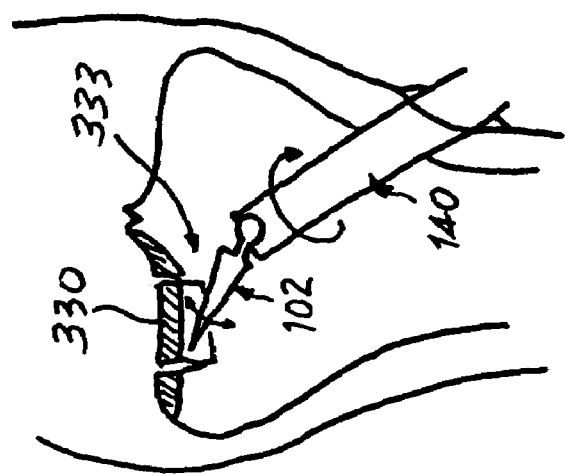
FIGS. 23 through 25 are diagrammatic illustrations of a procedure for reduction of the bone fracture in accordance with the present invention.
Figure 24:
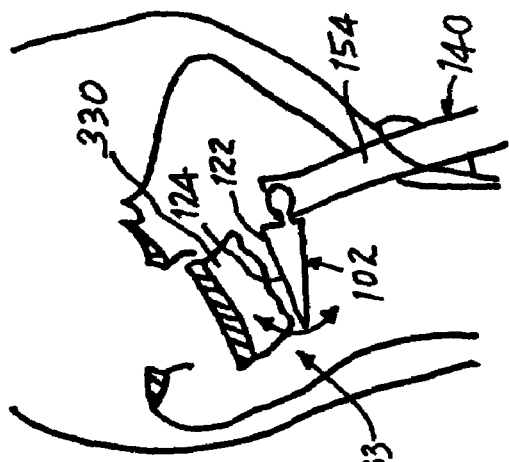

Instrument 140 is advanced along the access passage 342, with the assistance of sharp cutting edge 126 along forward edge 128 of the working head 102, until the forward edge 128 is placed beneath the far subchondral end 350 of the bone fracture fragment 330, as shown in FIG. 23. Then, the working head 102 is articulated relative to the stem 154 into a working configuration and the stem 154 is moved laterally somewhat to juxtapose the working head 102 with the bone fracture fragment 330 and to orient the working head 102 generally parallel with the bone fracture fragment 330, as shown in FIG. 24, wherein the rigid working face 122 of the working head 102 confronts the bone fracture fragment 330 with the broad flat working area 124, relative to the limited altitudinal thickness H of the working head 102 and the narrow, relatively small transverse dimensions of the stem 154. Through a combination of articulation of the working head 102 and manipulation of the stem 154, the bone fracture fragment 330 is engaged by the working head 102, along the broad flat working area 124 of the rigid working face 122, and is moved into the original anatomical position, as illustrated in FIG. 25, to complete the reduction of the bone fracture fragment 330 at the bone fracture site 333. Instrument 140 then is withdrawn from the bone fracture site 333, with the assistance of further cutting edge 130, if present.

Where a bone fracture fragment is more severely displaced, either instrument 190 or instrument 250 may be utilized in connection with the present invention. Thus, as shown in FIGS. 26A through 28B, instrument 250 is employed in accordance with the present invention to reduce a bone fracture fragment 350 which has been more severely displaced, in both anterior-posterior and lateral planes, at a bone fracture site 353. As described above in connection with the reduction procedure utilizing instrument 140, instrument 250 is inserted through a small incision 360 made through skin and subcutaneous tissue, opposite to the bone fracture fragment 350 to create an access passage 362 having a minimally invasive cross-sectional area and aligned with an access direction 364 leading to the bone fracture site 353. Instrument 250 is inserted into the incision 360, with the working head 102 in an insertion configuration wherein the working head 102 is aligned with longitudinal axis L and the insertion area 120 is oriented transverse to the access direction 364, the insertion area 120 being dimensioned and configured for passing through the minimally invasive cross-sectional area of the access passage 362 to move along the access passage 362 to the bone fracture site 353.

Instrument 250 is advanced along the access passage 362, with the assistance of sharp cutting edge 124 along forward end 126 of the working head 102, until the edge 124 is placed beneath the far subchondral end 370 of the bone fracture fragment 350, as shown in FIG. 26A, wherein bone fracture site 353 is illustrated in an anterior-posterior projection, and in 26B, wherein bone fracture site 353 is illustrated in a lateral projection. Then, the working head 102 is articulated relative to the stem 260, through rotation about both axes T and A, as well as axis L, into a working configuration and the stem 260 is advanced and moved laterally somewhat to place the working head 102 oriented generally parallel with the bone fracture fragment 350, as shown in FIGS. 27A and 27B, wherein the rigid working face 122 of the working head 102 confronts the bone fracture fragment 350 with the broad flat working area 124, relative to the narrow, relatively small transverse dimensions of the stem 260. Through a combination of articulation of the working head 102 and manipulation of the stem 260, the bone fracture fragment 350 is engaged by the working head 102, along the broad flat working area 124 of the rigid working face 122, and is moved into the appropriate anatomical position, as illustrated in FIGS. 28A and 28B, to complete the reduction of the bone fracture fragment 350 at the bone fracture site 353. Instrument 250 then is withdrawn from the bone fracture site 353, with the assistance of further cutting edge 130, if present.

Referring now to FIGS. 29 through 32, another instrument constructed in accordance with the present invention is illustrated at 400 and is seen to have a working head 402 and a stem 404, the stem 404 extending along a longitudinal axis L between a first end 406 connected to the working head 402 and a second end 408 remote from the working head 402. A connector 410 connects the working head 402 to the stem 404 at the first end 406 of the stem 404. A handle 412 adjacent the remote second end 408 enables manipulation of the instrument 400, as will be described in detail below.

Working head 402 is selectively actuated between an insertion configuration, shown in FIGS. 29 and 30, and a working configuration, illustrated in FIGS. 31 and 32. To that end, working head 402 is comprised of sections 420 extending axially essentially parallel to axis L from respective terminal ends 422 toward the second end 408 of the stem 404, the terminal ends 422 each including a sector 423. In the insertion configuration of the working head 402, the sections 420 are contracted radially toward one another such that the sectors 423 present a relatively small terminal area 424 transverse to longitudinal axis L, at the terminal end 425 of the working head 402, as illustrated in FIGS. 29 and 30, in comparison to a larger working area 426 made available when the sectors 423 are extended radially to establish an essentially rigid working face 428 across the terminal end 425 of the working head 402 in the working configuration as depicted in FIGS. 31 and 32.

Actuation of the working head 402 between the insertion configuration and the working configuration is accomplished by the selective operation of an actuating arrangement which includes a rod 430 extending along axis L from a forward end 432, through a central bore 434 in stem 404, to a rearward end 435. Rod 430 is slidable axially within bore 434 and is flared radially outwardly at the forward end 432 to establish camming surfaces 436 along the rod 430 adjacent forward end 432 and confronting sections 420 of the working head 402, which sections 420 are arranged circumferentially about the rod 430. In the insertion configuration of working head 402, the camming surfaces 436 adjacent forward end 432 of rod 420 are located relative to the sections 420 of the working head 402 to enable the sections 420 to remain contracted, as shown in FIGS. 29 and 30. The rearward end 435 of the rod 430 extends axially beyond the second end 408 of stem 404 and includes a threaded portion 440 engaged with a complementary threaded knob 442 which, together with rod 420, comprise an actuator for moving the working head 402 between the insertion configuration and the working configuration. Thus, upon advancement of knob 442 along threaded portion 440, against second end 408 of stem 404, rod 420 is drawn rearwardly to engage camming surfaces 436 with the surrounding sections 420 and the sections 420 are moved radially outwardly to establish the working configuration of working head 402, as depicted in FIGS. 31 and 32. The sections 420 are constructed of a resiliently deflectable material, such as a resiliently flexible steel or a somewhat renitent or reinforced synthetic polymeric material, enabling axial displacement of rod 430 to result in movement the sections 420 between the radially contracted and radially expanded positions of the sections 420 corresponding respectively to the insertion configuration and the working configuration of the working head 402.

Figure 33:
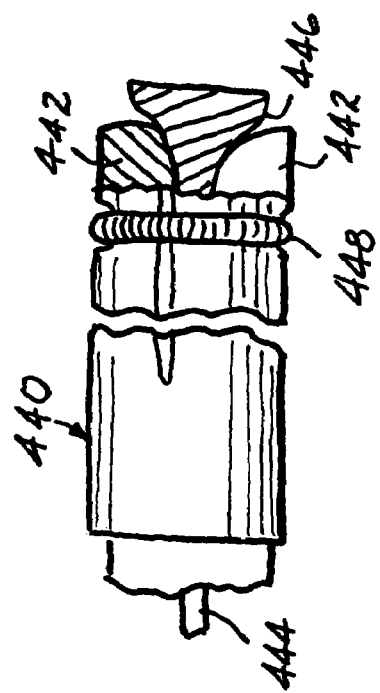
FIG. 33 is a fragmentary plan view showing alternate component parts of the instrument.
Figure 37:
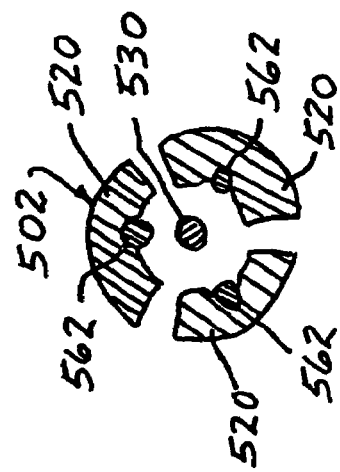
FIG. 37 is a transverse cross-sectional view taken along line 37-37 of FIG. 35.
Figure 34:
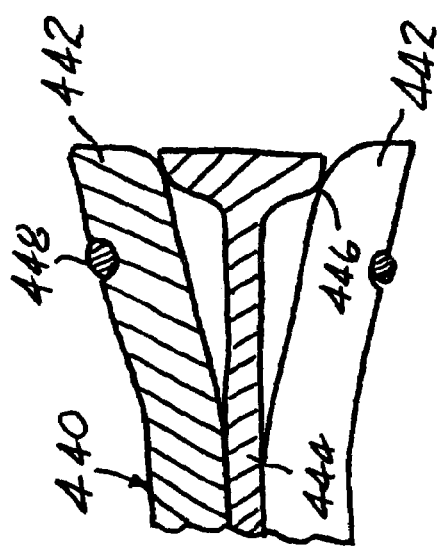
FIG. 34 is a fragmentary longitudinal cross-sectional view of a portion of FIG. 33 and showing the alternate component parts in another operating configuration.
Figure 36:
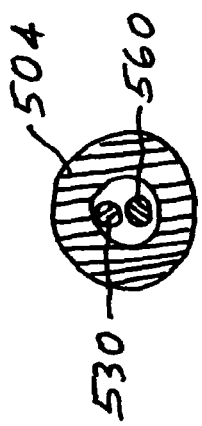
FIG. 36 is a transverse cross-sectional view taken along line 36-36 of FIG. 35.

Turning now to FIGS. 33 and 34, an alternate working head 440 includes sections 442 arranged circumferentially about a rod 444 having camming surfaces 446, as described above. However, working head 440 further includes a biasing arrangement in the form of a resiliently expandable band 448 which biases the sections 442 toward the insertion configuration, as seen in FIG. 33, and allows selective deflection of the sections 442 radially outwardly into the working position, as depicted in FIG. 34, in response to axial movement of rod 444 in a rearward direction. Thus, rather than relying upon sections constructed of a resiliently deflectable material for biasing the sections radially inwardly, sections 442 may be constructed of a more rigid material and may be arranged for ready radial displacements, biased radially inwardly by band 448.

In the embodiment illustrated in FIGS. 35 through 39, an alternate instrument constructed in accordance with the invention is illustrated at 500 and is seen to have a working head 502 and a stem 504, the stem 504 extending along a longitudinal axis L between a first end 506 connected to the working head 502 and a second end 508 remote from the working head 502. A connector 510 connects the working head 502 to the stem 504 at the first end 506 of the stem 504. A handle 512 adjacent the remote second end 508 enables manipulation of the instrument 500, in a manner described in detail below.

Working head 502 is actuated between an insertion configuration and a working configuration by moving sections 520 between radially contracted positions, as illustrated in FIG. 38, and radially expanded positions, as seen in FIG. 39. An actuating arrangement includes a rod 530 extending longitudinally along a central bore 532 in the stem 504 and flared adjacent a forward end 534 to provide camming surfaces 536 confronting the sections 520. Rod 530 is coupled at 538 to an actuator in the form of a lever 540 mounted for pivotal movement about a pin 542 adjacent the remote second end 508 of the stem 504. Upon pivoting lever 540 in the direction of arrow 544 in FIG. 35, rod 530 is drawn rearwardly, engaging camming surfaces 536 with sections 520 and moving the sections 520 radially outwardly. A locking mechanism includes a lock bar 550 biased by a spring 552 into engagement with one of several notches 554 fixed relative to stem 504 so that lever 540 is secured in place and working head 502 is fixed in the working configuration.

Upon release of lock bar 550 and pivoting of lever 540 in the direction of arrow 556, a cable 560, coupled to lever 540 for movement with the lever 540, is drawn rearwardly, along central bore 532, while rod 530 simultaneously is moved forward. Cable 560 is divided into branches 562 spaced apart circumferentially and diverging radially adjacent working head 502 and each branch 562 is attached to a corresponding section 520 so that as the camming surfaces 536 are moved forward with forward movement of rod 530, the branches 562 of cable 560 are drawn rearwardly, with the result that sections 520 are contracted radially relative to one another and working head 502 is returned to the insertion configuration, as illustrated in FIG. 38. In this manner, sections 520 are moved through positive displacements which do not require that the sections 520 be constructed of a resilient material or be biased by a resiliently biasing mechanism. Again, lock bar 550 is engaged with a notch 554 to secure lever 540 in place and fix working head 502 in the insertion configuration.

An alternate stem construction, available for use in connection with any of the aforesaid instruments, is illustrated in FIGS. 40 through 42 wherein an instrument 600 includes a stem 602 extending between a working head connected to the stem 602 by a connector 610 adjacent a first end 612 of the stem 602, and a handle 614 adjacent a second end 616 of the stem 602. Although the working head may be in the form of any one of the working heads 102, 402, and 502 described above, connected at connector 610, the alternate stem construction is illustrated in use with working head 402 described above in connection with the instrument 400 illustrated in FIGS. 29 through 42, and component parts of instrument 400 are repeated in the instrument depicted in FIGS. 40 through 42.

Stem 602 is an articulating stem and comprises a plurality of segments 620 placed serially along a longitudinal axis L, and a manipulating arrangement includes a manipulator 622 at a remote actuating site 624 for selectively moving the segments 620 relative to one another in directions transverse to axis L to articulate the stem 602 and guide the working head 402 along a selected path of alternate paths extending from the remote actuation site 624 to a bone fracture site. Each segment 620 engages a next-consecutive segment 620 at a joint 630 between abutting segments 620. Each joint 630 includes a concave semi-spherical socket 632 in one segment 620 engaged by a complementary convex semi-spherical protrusion 634 on a consecutive segment 620. The jointed stem 602 thus is selectively articulated between the straight configuration illustrated in FIG. 40 and curved configurations, one of which is shown in FIG. 42.

Articulation of stem 602 is attained by lateral movements of the segments 620 relative to one another, effected by cables 640 anchored to a forward-most segment 620F at anchoring points 642 and extending through corresponding passages 644 from the anchoring points 642 to the manipulator 622. The cables 640, and corresponding passages 644, are arranged circumferentially about central longitudinal axis L and are spaced laterally from axis L such that upon manipulation of the cables 640, segments 620 respond with corresponding lateral movements to be articulated to a selected configuration for following a selected path which can be either linear or non-linear, as will be described below. Manipulator 622 is shown in the form of a joy-stick arrangement in which a control lever 650 is mounted upon the stem 602 by means of a ball joint 652 and is coupled to the cables 654 such that manipulation of the control lever 650 will move the cables through differential longitudinal displacements to effect articulation of the stem 602 into the various stem configurations. A locking mechanism includes a lock bar 660 for securing the manipulator 622 against inadvertent actuation which might otherwise move the segments 620 away from a selected stem configuration.

Turning now to FIGS. 43 through 48, the reduction of an intra-articular fracture in accordance with the present invention is illustrated somewhat diagrammatically in connection with a tibial plateau fracture, utilizing instrument 400, described above in connection with FIGS. 29 through 32. Subsequent to the exact location and orientation of bone fracture fragment 670 and an appropriate approach for reduction of the bone fracture fragment 670 at bone fracture site 672, as determined by radiographs or by alternate imaging methods, which provide images similar to those represented in FIGS. 43 through 45, a small incision 674 is made through skin and subcutaneous tissue, distal and aligned with bone fracture fragment 670. A drill bit 680 having a diameter slightly larger than working head 402 of instrument 400, in the insertion configuration of the working head 402, is introduced through incision 674 and is advanced toward bone fracture fragment 670 to establish an access passage 682 having a minimally invasive cross-sectional area and aligned with an access direction 684 leading to the bone fracture site 672.

Subsequent to retraction of drill bit 680, instrument 400 is inserted into the incision 674, with the working head 402 in an insertion configuration wherein the sections 420 of the working head 402 are contracted radially toward one another to present the relatively small terminal area 424 transverse to longitudinal axis L, the terminal area 424 being dimensioned and configured for passing through the minimally invasive cross-sectional area of the access passage 682 to move along the access passage 682 to the bone fracture site 672, as seen in FIG. 45.

Upon reaching a position just beneath the bone fracture fragment 670, as depicted in FIG. 46, the working head 402 is actuated into the working configuration, with sections 420 moved radially outwardly to establish the larger working area 426 made available across the working face 428 of the working head 402 in the working configuration. Instrument 400 then is advanced longitudinally, in a direction along axis L, to move the bone fracture fragment 670 into an appropriate anatomical position in bone fracture gap 686, as seen in FIG. 47. With the bone fracture fragment 670 thus reduced, the sections 420 of the working head 402 are contracted radially to return the working head 402 to the insertion configuration and the instrument 400 is retracted, as seen in FIG. 48, to be withdrawn through the incision 674 for completion of the procedure.

Figure 51:
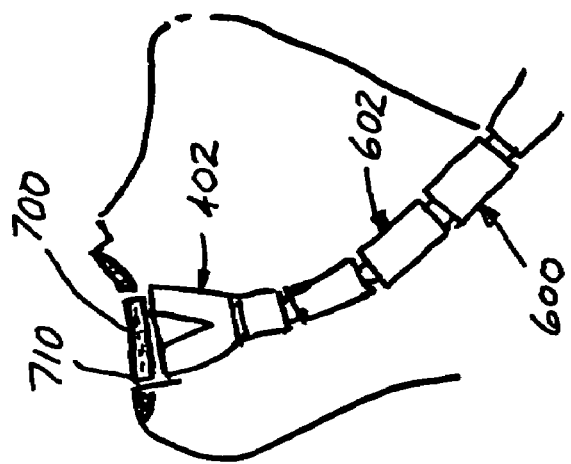
FIGS. 49 through 51 are diagrammatic views illustrating another procedure for reduction of a bone fracture, conducted in accordance with the present invention.
Figure 50:
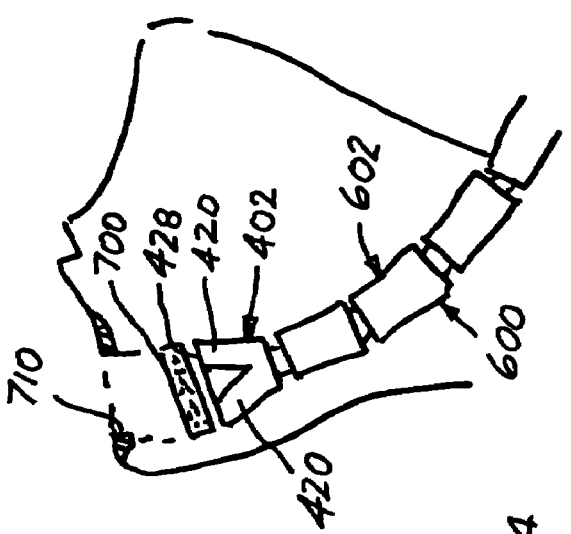
Figure 49:
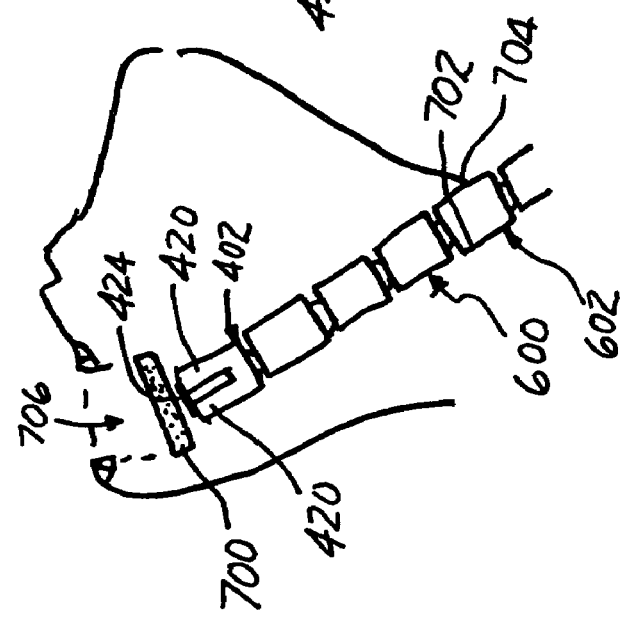

The reduction of a tilted bone fracture fragment 700 is accomplished, in accordance with the present invention, utilizing instrument 600 having articulated stem 602 (see FIGS. 40 through 42), as shown in FIGS. 49 through 51. In order to gain better access to tilted bone fracture fragment 700, an access passage 702 is established through bony surface 704 opposite bone fracture site 706, utilizing a drill (not shown). Instrument 600 is introduced into access passage 702 with working head 402 in the insertion configuration, that is, with sections 420 contracted radially to present the small terminal area 424, and with the segments 620 of the stem 602 aligned essentially along a straight line so that the stem 602 is in an essentially straight configuration, as seen in FIG. 49, capable of being guided along a direct linear path toward the bone fracture fragment 700. Upon being juxtaposed in close proximity with the bone fracture fragment 700, the working head 402 is actuated into the working configuration by deploying the sections 420 radially outwardly, as seen in FIG. 50, and the stem 602 is articulated into a curved configuration for being guided along a selected non-linear path so as to gain an optimum orientation of the working head 402 for engaging the bone fracture fragment 700 with the working face 428 of the working head 402.

Once the working face 428 is engaged with the bone fracture fragment 700, instrument 600 is advanced toward bone fracture gap 710 while stem 602 is articulated to gradually increase the curvature of the stem 602 so as to be guided along a selected non-linear path to facilitate maneuvering the bone fracture fragment 700 in attaining an appropriate anatomical fit of the bone fracture fragment within the bone fracture gap 710, as depicted in FIG. 51. Subsequently, working head 402 is returned to the insertion configuration, stem 602 is returned to an essentially straight configuration, and instrument 600 is withdrawn through access passage 702 for completion of the procedure.

It will be apparent that the present invention attains the several objects and advantages summarized above, namely: Enables minimally invasive procedures for the reduction of bone fractures by virtue of requiring only small openings in soft tissue and bone for the introduction, manipulation and removal of instruments constructed for carrying out percutaneous techniques for bone fracture reduction; provides instruments having broad working configurations relative to narrow insertion configurations to accomplish effective support and movement of bone fracture fragments into reduced positions at a bone fracture site accessed through a minimally invasive access passage; allows for simplified manipulation of a working head from a remote location to rotate and translate bone fracture fragments in multiple directions for minimally invasive bone fracture reduction, and especially in the management of bone fractures and bone conditions located near joints of the body (peri-articular fractures) and fractures that involve joint surfaces (intra-articular fractures); allows the reduction of relatively large fractured joint surfaces, percutaneously, using only arthroscopic or radiographic visualization methods in minimally invasive procedures; avoids risks and complications which otherwise could arise out of open reduction procedures, such as soft tissue necrosis and bone infections; reduces operating times and blood loss; enables a reduction in the length of a hospital stay and, in some instances, avoids hospitalization entirely; reduces recovery time and patient discomfort; avoids excessive joint stiffness and potentially serious functional restrictions affecting daily living, as well as work and recreational pursuits.

It is to be understood that the above detailed description of preferred embodiments of the invention are provided by way of example only. Various details of design, construction and procedure may be modified without departing from the true spirit and scope of the invention, as set forth in the appended claims.

The embodiments of the invention in which an exclusive property or privilege is claimed are defined as follows:

1. Apparatus for the reduction of a bone fragment of a bone fracture at a bone fracture site through a minimally invasive access passage to the bone fracture site, the access passage following an access direction and having a minimally invasive cross-sectional area, the apparatus comprising:
   a working head constructed for actuation between an insertion configuration and a working configuration;
   the insertion configuration providing the working head with an insertion area transverse to the access direction and being dimensioned and configured for passing through the minimally invasive cross-sectional area to move along the access passage to the bone fracture site;
   the working configuration providing the working head with an essentially rigid working face extending over a working area transverse to the access direction, the working area of the extended working face being substantially greater than the insertion area for engaging and manipulating the bone fragment into a reduced position;
   an actuating arrangement including an actuator remote from the working head for actuating the working head between the insertion configuration and the working configuration from an actuating site remote from the bone fracture site;
   a coupling arrangement coupling the actuator with the working head for enabling remote actuation of the working head in response to operation of the actuator; and
   a manipulating arrangement for selective manipulation of the working head from the remote actuating site such that insertion of the working head through the access passage to the bone fracture site is accomplished with the working head in the insertion configuration, and upon placement of the working head at the bone fracture site and actuation of the working head to the working configuration, reduction of the bone fragment is accomplished with the working head in the working configuration to engage the bone fragment with the working face and manipulate the bone fragment into the reduced position at the bone fracture site;
   the manipulating arrangement including a stem extending longitudinally along a longitudinal axis and having lateral transverse dimensions; and
   the working head comprising a blade-like member having a leading edge, a trailing edge spaced longitudinally from the leading edge, an altitudinal thickness, and side edges spaced apart laterally from one another along a lateral dimension substantially greater than the laterally transverse dimensions of the stem such that the working face extends over the working area between the leading, trailing and side edges throughout a relatively large area in comparison to any area established by the laterally transverse dimensions of the stem and the thickness of the blade-like member.

2. The apparatus of claim 1 wherein the manipulating arrangement includes a stem extending along a longitudinal axis between the actuator and the working head, the stem comprising a plurality of segments placed serially along the longitudinal axis, and a manipulator for selectively moving the segments relative to one another transverse to the longitudinal axis to guide the stem along a selected path of selectable alternate paths, both linear and non-linear, between the actuating site and the bone fracture site.

3. The apparatus of claim 2 wherein the manipulator includes control cables extending along the segments between the actuator and the working head for moving the segments transversely relative to one another.

4. The apparatus of claim 1 wherein:
   the actuating arrangement includes a pivotal connection between the blade-like member and the stem for selective pivotal movement of the blade-like member, in response to operation of the actuator, between an insertion position, wherein the working face extends longitudinally, essentially aligned with the longitudinal axis of the stem for passing the blade-like member along the access direction to the bone fracture site, and a working position, wherein the working area extends transverse to the longitudinal axis for engaging the working face with the bone fragment and reduction of the bone fragment of the bone fracture at the bone fracture site.

5. The apparatus of claim 4 wherein the pivotal connection includes a hinge for enabling selective movement of the blade-like member transverse to the longitudinal axis to place the working face in a working position selected from transverse positions of the blade-like member relative to the longitudinal axis.

6. The apparatus of claim 4 wherein the pivotal connection includes a ball-joint for enabling selective movement of the blade-like member in lateral and altitudinal directions relative to the longitudinal axis to place the working face in a working position selected from lateral and altitudinal positions of the blade-like member relative to the longitudinal axis.

7. The apparatus of claim 4 wherein the leading edge includes a cutting edge for facilitating advancement of the blade-like member along the insertion direction when the blade-like member is in the insertion position.

8. The apparatus of claim 4 wherein the stem includes a plurality of segments placed serially along the longitudinal axis, and the manipulation arrangement includes a manipulator for selectively moving the segments relative to one another transverse to the longitudinal axis to guide the stem along a selected path of selectable alternate paths, both linear and non-linear, between the actuating site and the bone fracture site.

9. The apparatus of claim 8 wherein the manipulator includes control cables extending along the segments between the actuator and the working head and coupled with the segments for moving the segments transversely relative to one another.

10. The apparatus of claim 9 wherein the segments include a forward-most segment coupled to the connector and the control cables are coupled to the forward-most segment and extending along the segments between the actuator and the forward-most segment for moving the segments transversely relative to one another.

11. The apparatus of claim 1 the working head comprises:
   a rod extending along a longitudinal axis;
   sections extending axially from respective terminal ends toward the remote actuating site, the sections being arranged circumferentially about the rod and terminating at transverse facial sectors establishing a terminal area at the respective terminal ends of the sections;
   camming surfaces on the rod, the camming surfaces being engaged with the sections for selectively moving the sections radially, in response to axial movement of the rod relative to the sections, between insertion positions, wherein the sections are contracted radially toward one another to present a relatively small terminal area transverse to the longitudinal axis, in comparison to the working area, the relatively small terminal area being dimensioned and configured for facilitating passage of the sections along the insertion direction to the bone fracture site, and working positions wherein the sections are moved radially outwardly away from one another to establish a relatively larger terminal area such that the facial sectors extend along the relatively larger working area for engaging the bone fragment and reducing the bone fragment of the bone fracture.

12. The apparatus of claim 11 wherein the working head includes a biasing arrangement for biasing the sections radially inwardly toward one another and into the insertion positions.

13. The apparatus of claim 11 wherein the manipulating arrangement includes a stem extending along a longitudinal axis between the actuator and the working head, the stem comprising a plurality of segments placed serially along the longitudinal axis, and a manipulator for selectively moving the segments relative to one another transverse to the longitudinal axis to guide the stem along a selected path of selectable alternate paths including both linear paths and non-linear paths, between the actuating site and the bone fracture site.

14. The apparatus of claim 13 wherein the manipulator includes control cables extending along the segments between the actuator and the working head for moving the segments transversely relative to one another.

15. Apparatus for the reduction of a bone fragment of a bone fracture at a bone fracture site through a minimally invasive access passage to the bone fracture site, the access passage following an access direction and having a minimally invasive cross-sectional area, the apparatus comprising:
a working head constructed for being moved between an insertion configuration and a working configuration;
the insertion configuration providing the working head with an insertion area transverse to the access direction and being dimensioned and configured for passing through the minimally invasive cross-sectional area to move along the access passage to the bone fracture site;
the working configuration providing the working head with an essentially rigid working face extending over a working area transverse to the access direction, the working area of the extended working face being substantially greater than the insertion area for engaging and maneuvering the bone fragment into a reduced position; and
a manipulating arrangement including a manipulator for selective manipulation of the working head from a remote manipulating site such that insertion of the working head through the access passage to the bone fracture site is accomplished with the working head in the insertion configuration, and upon placement of the working head at the bone fracture site and movement of the working head in the working configuration, reduction of the bone fragment is accomplished with the working head in the working configuration to engage the bone fragment with the working face and maneuver the bone fragment into the reduced position at the bone fracture site;
the manipulating arrangement including a stem extending longitudinally along a longitudinal axis and having lateral transverse dimensions; and
the working head comprising a blade-like member having a leading edge, a trailing edge spaced longitudinally from the leading edge, an altitudinal thickness, and side edges spaced apart laterally from one another along a lateral dimension substantially greater than the laterally transverse dimensions of the stem such that the working face extends over the working area between the leading, trailing and side edges throughout a relatively large area in comparison to any area established by the laterally transverse dimensions of the stem and the thickness of the blade-like member.

16. The apparatus of claim 15 wherein the manipulating arrangement includes a stem extending along a longitudinal axis between the manipulator and the working head, the stem comprising a plurality of segments placed serially along the longitudinal axis, and a further manipulator for selectively moving the segments relative to one another transverse to the longitudinal axis to guide the stem along a selected path of selectable alternate paths, both linear and non-linear, between the remote manipulating site and the bone fracture site.

17. The apparatus of claim 16 wherein the manipulator includes control cables extending along the segments between the manipulating site and the working head for moving the segments transversely relative to one another.

18. The apparatus of claim 15 wherein the leading edge includes a cutting edge for facilitating advancement of the blade-like member along the access direction when the blade-like member is in the insertion position.

19. A method for the reduction of a bone fragment of a bone fracture at a bone fracture site through a minimally invasive access passage to the bone fracture site, the access passage following an access direction and having a minimally invasive cross-sectional area, the method comprising:
introducing into the access passage a working head constructed for actuation between an insertion configuration and a working configuration;
the insertion configuration providing the working head with an insertion area transverse to the access direction and being dimensioned and configured for passing through the minimally invasive cross-sectional area to move along the access passage to the bone fracture site; and
the working configuration providing the working head with an essentially rigid working face extended over a working area transverse to the access direction, the working area of the extended working face being substantially greater than the insertion area for engaging and manipulating the bone fragment into a reduced position;
with the working head in the insertion configuration, passing the working head through the minimally invasive cross-sectional area to move the working head along the access passage and place the working head at the bone fracture site;
actuating an actuator remote from the working head to actuate the working head from the insertion configuration into the working configuration from an actuating site remote from the bone fracture site; and
selectively manipulating the working head from the remote actuating site with a manipulating arrangement including a stem extending longitudinally along a longitudinal axis and having lateral transverse dimensions, the working head comprising a blade-like member having a leading edge, a trailing edge spaced longitudinally from the leading edge, an altitudinal thickness, and side edges spaced apart laterally from one another along a lateral dimension substantially greater than the laterally transverse dimensions of the stem so that the working face extends over the working area between the leading, trailing and side edges throughout a relatively large area in comparison to any area established by the laterally transverse dimensions of the stem and the thickness of the blade-like member such that insertion of the working head through the access passage to the bone fracture site is accomplished with the working head in the insertion configuration and, upon placement of the working head at the bone fracture site and actuation of the working head to the working configuration, reduction of the bone fragment is accomplished with the working head in the working configuration to engage the bone fragment with the working face and manipulate the bone fragment into the reduced position at the bone fracture site.

20. The method of claim 19 including guiding the working head along a selected path of alternate paths, both linear and non-linear, between the remote actuating site and the bone fracture site to maneuver the engaged bone fragment into the reduced position.

* * * * *